United States Patent
Agarwal et al.

(10) Patent No.: US 10,188,434 B2
(45) Date of Patent: Jan. 29, 2019

(54) HYBRID MULTIFUNCTIONAL POSTERIOR INTERSPINOUS FUSION DEVICE

(71) Applicant: The University of Toledo, Toledo, OH (US)

(72) Inventors: Anand K. Agarwal, Ottawa Hills, OH (US); Vijay K. Goel, Holland, OH (US); Aakash Agarwal, Ottawa Hills, OH (US)

(73) Assignee: The University of Toledo, Toledo, OH (US)

( * ) Notice: Subject to any disclaimer, the term of this patent is extended or adjusted under 35 U.S.C. 154(b) by 496 days.

(21) Appl. No.: 14/379,139

(22) PCT Filed: Feb. 19, 2013

(86) PCT No.: PCT/US2013/026665
§ 371 (c)(1),
(2) Date: Aug. 15, 2014

(87) PCT Pub. No.: WO2013/123497
PCT Pub. Date: Aug. 22, 2013

(65) Prior Publication Data
US 2015/0012040 A1 Jan. 8, 2015

Related U.S. Application Data

(60) Provisional application No. 61/599,988, filed on Feb. 17, 2012.

(51) Int. Cl.
*A61B 17/70* (2006.01)

(52) U.S. Cl.
CPC ...... *A61B 17/7068* (2013.01); *A61B 17/7062* (2013.01)

(58) Field of Classification Search
CPC .............. A61B 17/7068; A61B 17/7062
(Continued)

(56) References Cited

U.S. PATENT DOCUMENTS

| 5,645,599 A * | 7/1997 | Samani | A61B 17/7062 606/248 |
| 6,743,257 B2 * | 6/2004 | Castro | A61F 2/442 623/17.16 |

(Continued)

FOREIGN PATENT DOCUMENTS

| CN | 101332116 A | 12/2008 |
| CN | 101708128 A | 5/2010 |

(Continued)

OTHER PUBLICATIONS

PCT International Search Report, Application No. PCT/US2013/026665, dated Apr. 19, 2013.
(Continued)

*Primary Examiner* — Ellen C Hammond
(74) *Attorney, Agent, or Firm* — MacMillan, Sobanski & Todd, LLC

(57) ABSTRACT

This invention relates to an improved structure for an interspinous stabilization device that more evenly distributes loads throughout the adjacent vertebrae than known interspinous stabilization devices, and further readily compensates for graft settling so as to maintain continued axial loading of the graft. More specifically, this invention relates to a medical device that helps in performing a spinal fusion procedure by holding the bone graft in place and stabilizing the facet screw by a plate that is attached to it. The invention also performs a dynamic function that compensates for settling of the bone graft over time. This dynamic function may, if desired, be enhanced by a movement-limiting mechanism that allows extension but not flexion such that (Continued)

the bone graft fusion remains in contact and fusion takes place.

10 Claims, 29 Drawing Sheets

(58) Field of Classification Search
    USPC .................................................. 606/247–249
    See application file for complete search history.

(56) References Cited

U.S. PATENT DOCUMENTS

| | | | | |
|---|---|---|---|---|
| 8,038,713 B2* | 10/2011 | Ferree | ..................... | A61F 2/442 623/17.11 |
| 8,348,977 B2 | 1/2013 | Bruneau et al. | | |
| 8,430,911 B2* | 4/2013 | Chin | .................. | A61B 17/7065 606/248 |
| 8,496,688 B2* | 7/2013 | Wang | ................. | A61B 17/7059 606/249 |
| 8,603,176 B2* | 12/2013 | Duplessis | ............... | A61F 2/442 623/17.11 |
| 9,173,686 B2* | 11/2015 | Sheffer | .............. | A61B 17/7062 |
| 9,247,968 B2* | 2/2016 | Taber | ................. | A61B 17/7068 |
| 9,370,382 B2* | 6/2016 | Thalgott | ............. | A61B 17/7062 |
| 9,381,047 B2* | 7/2016 | Sheffer | .............. | A61B 17/7062 |
| 9,510,872 B2* | 12/2016 | Donner | ............. | A61B 17/7026 |
| 2002/0049497 A1* | 4/2002 | Mason | .................... | A61F 2/447 623/17.11 |
| 2004/0006343 A1* | 1/2004 | Sevrain | .............. | A61B 17/7059 606/279 |
| 2006/0241601 A1* | 10/2006 | Trautwein | ........... | A61B 17/7049 606/248 |
| 2007/0100340 A1* | 5/2007 | Lange | ................. | A61B 17/7065 606/279 |
| 2007/0161992 A1* | 7/2007 | Kwak | ................. | A61B 17/7065 606/249 |
| 2007/0161993 A1* | 7/2007 | Lowery | .............. | A61B 17/7055 606/279 |
| 2008/0228225 A1* | 9/2008 | Trautwein | .......... | A61B 17/1606 606/246 |
| 2009/0149886 A1* | 6/2009 | Zentes | ................ | A61B 17/7065 606/249 |
| 2009/0270919 A1* | 10/2009 | Dos Reis, Jr. | ...... | A61B 17/7062 606/249 |
| 2010/0070037 A1* | 3/2010 | Parry | ................. | A61B 17/7059 623/17.16 |
| 2010/0094346 A1 | 4/2010 | Matityahu | | |
| 2010/0145386 A1 | 6/2010 | Greenhalgh et al. | | |
| 2011/0029020 A1* | 2/2011 | Gordon | .............. | A61B 17/7062 606/248 |
| 2011/0040330 A1* | 2/2011 | Sheffer | .............. | A61B 17/7062 606/249 |
| 2011/0172711 A1 | 7/2011 | Kirschman | | |
| 2011/0224740 A1 | 9/2011 | Smisson, III et al. | | |
| 2011/0238114 A1* | 9/2011 | Lim | .................... | A61B 17/7065 606/248 |
| 2011/0313458 A1* | 12/2011 | Butler | ................. | A61B 17/7065 606/249 |
| 2012/0065683 A1* | 3/2012 | Kuo | .................... | A61B 17/7065 606/248 |
| 2012/0226312 A1* | 9/2012 | Thalgott | ............. | A61B 17/7062 606/246 |
| 2013/0023933 A1* | 1/2013 | Haas | .................. | A61B 17/7065 606/248 |
| 2013/0023934 A1* | 1/2013 | Haas | .................. | A61B 17/7065 606/249 |
| 2013/0041408 A1* | 2/2013 | Dinville | ............. | A61B 17/7065 606/249 |
| 2014/0188170 A1* | 7/2014 | Zappacosta | ........ | A61B 17/7062 606/249 |
| 2014/0228886 A1* | 8/2014 | Aflatoon | ............. | A61B 17/7065 606/249 |

FOREIGN PATENT DOCUMENTS

| | | |
|---|---|---|
| EP | 1872731 A1 | 1/2008 |
| WO | 2006110578 A2 | 10/2006 |
| WO | 2011005508 A2 | 1/2011 |
| WO | 2011007251 A2 | 1/2011 |
| WO | 2013123497 A1 | 8/2013 |

OTHER PUBLICATIONS

PCT Written Opinion, Application No. PCT/US2013/026665, dated Apr. 19, 2013.
European Supplementary Search Report, Application No. EP 13749229.4, dated Dec. 4, 2015.

* cited by examiner

HYBRID MULTIFUNCTIONAL POSTERIOR INTERSPINOUS FUSION DEVICE

CROSS-REFERENCE TO RELATED APPLICATIONS

This application claims the benefit of U.S. Provisional Application No. 61/599,988, filed Feb. 17, 2012, the disclosure of which is incorporated herein by reference.

STATEMENT REGARDING FEDERALLY SPONSORED RESEARCH OR DEVELOPMENT

Not applicable.

BACKGROUND OF THE INVENTION

This invention relates in general to an improved structure for a hybrid multifunctional posterior interspinous fusion device.

An interspinous stabilization device is a device that is adapted to be secured to two or more adjacent vertebrae of a spine in order to stabilize the relative positioning therebetween. An interspinous stabilization device can also be used to facilitate the placement of a bone-growth material, such as a bone graft material, between such adjacent vertebrae to enhance bone growth and promote fusion of the adjacent vertebrae.

Wolff's law of dynamic osteosynthesis states that every change in the function of a bone is followed by definitive changes in its internal architecture and secondary alterations in its external confirmation. This means that osseous tissues remodel in direct response to the stresses placed upon them. Although known interspinous stabilization devices have functioned satisfactorily for stabilizing the relative positioning of the adjacent vertebrae to which they are connected, they are not well suited for desirably maintaining axial compression on a bone graft material that is disposed between such adjacent vertebrae after graft settling occurs, such as described in Wolff's law. Thus, it would be desirable to provide an improved structure for an interspinous stabilization device that more evenly distributes loads throughout the adjacent vertebrae than known structures, and further readily compensates for graft settling so as to maintain continued axial loading of the graft.

SUMMARY OF THE INVENTION

This invention relates to an improved structure for an interspinous stabilization device that more evenly distributes loads throughout the adjacent vertebrae than known interspinous stabilization devices, and further readily compensates for graft settling so as to maintain continued axial loading of the graft.

More specifically, this invention relates to a medical device that helps in performing a spinal fusion procedure by holding the bone graft in place and stabilizing the facet screw by a plate that is attached to it. The invention also performs a dynamic function that compensates for settling of the bone graft over time. This dynamic function may, if desired, be enhanced by a movement-limiting mechanism that allows extension but not flexion such that the bone graft fusion remains in contact and fusion takes place. Thus, the interspinous stabilization device of this invention is a multipurpose device that both more evenly distributes loads throughout the adjacent vertebrae than known interspinous stabilization devices, and further readily compensates for graft settling so as to maintain continued axial loading of the graft. A mounting plate of the interspinous fusion device may be secured to a body portion therein in either a fixed or poly-axial manner so as to provide better stability in lateral bending and rotation.

Some of the indications for use of the interspinous fusion device of this invention may include: (1) supplemental fixation for anterior lumbar interbody fusion (ALIF) procedures; (2) supplemental fixation for transforaminal lumbar interbody fusion TLIP) procedures; (3) supplemental fixation lateral interbody fusion procedures; (4) posterior interlaminar fusion; (5) posterolateral fusion; (6) fusion in pars defect with facet pedicular screw; (7) fusion in Grade I spondolystheis; and (8) revision option in failed fusion/hybrid constructs.

Various aspects of this invention will become apparent to those skilled in the art from the following detailed description of the various embodiments of the invention, when read in light of the accompanying drawings.

DESCRIPTION OF THE EMBODIMENTS

Figure 1:
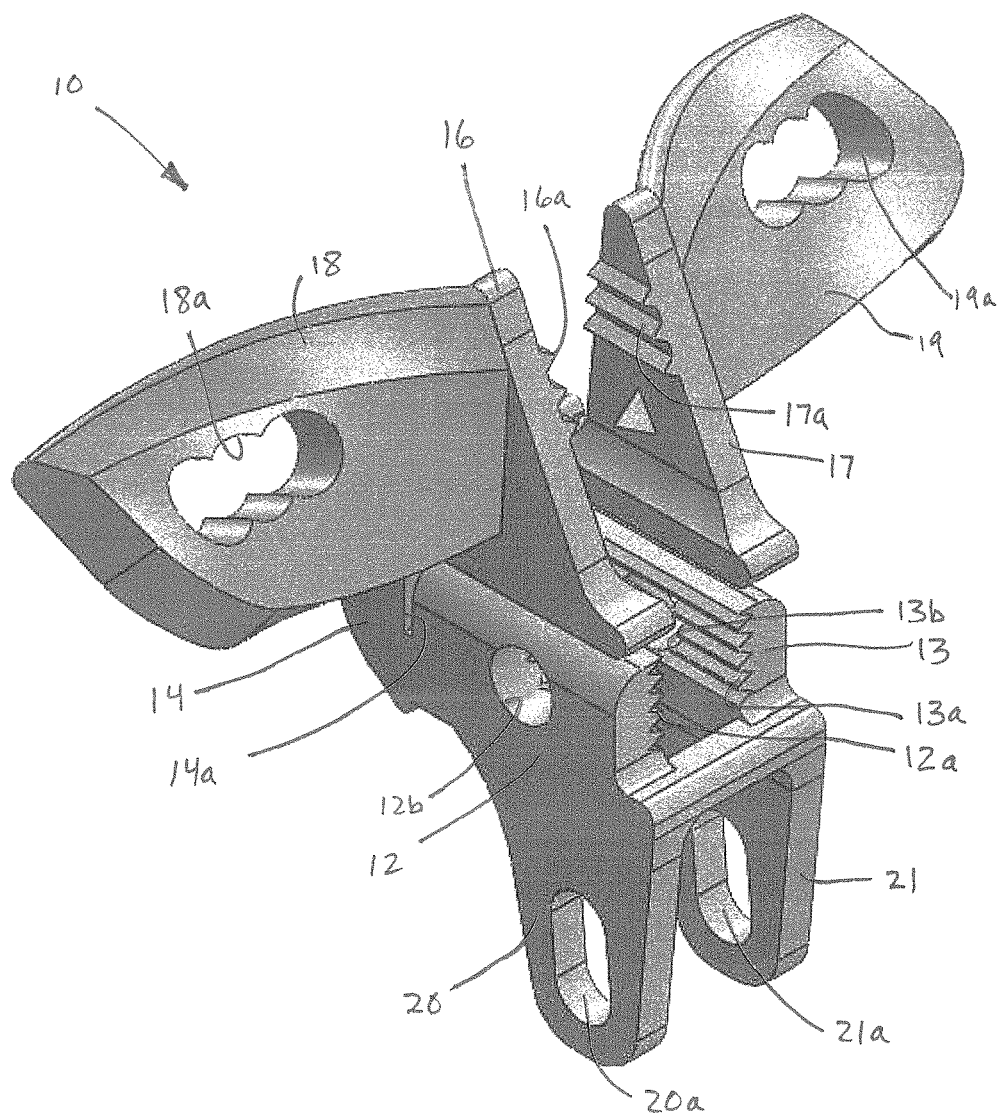
FIG. 1 is a perspective view of a first embodiment of an interspinous fusion device in accordance with this invention.
Figure 2:
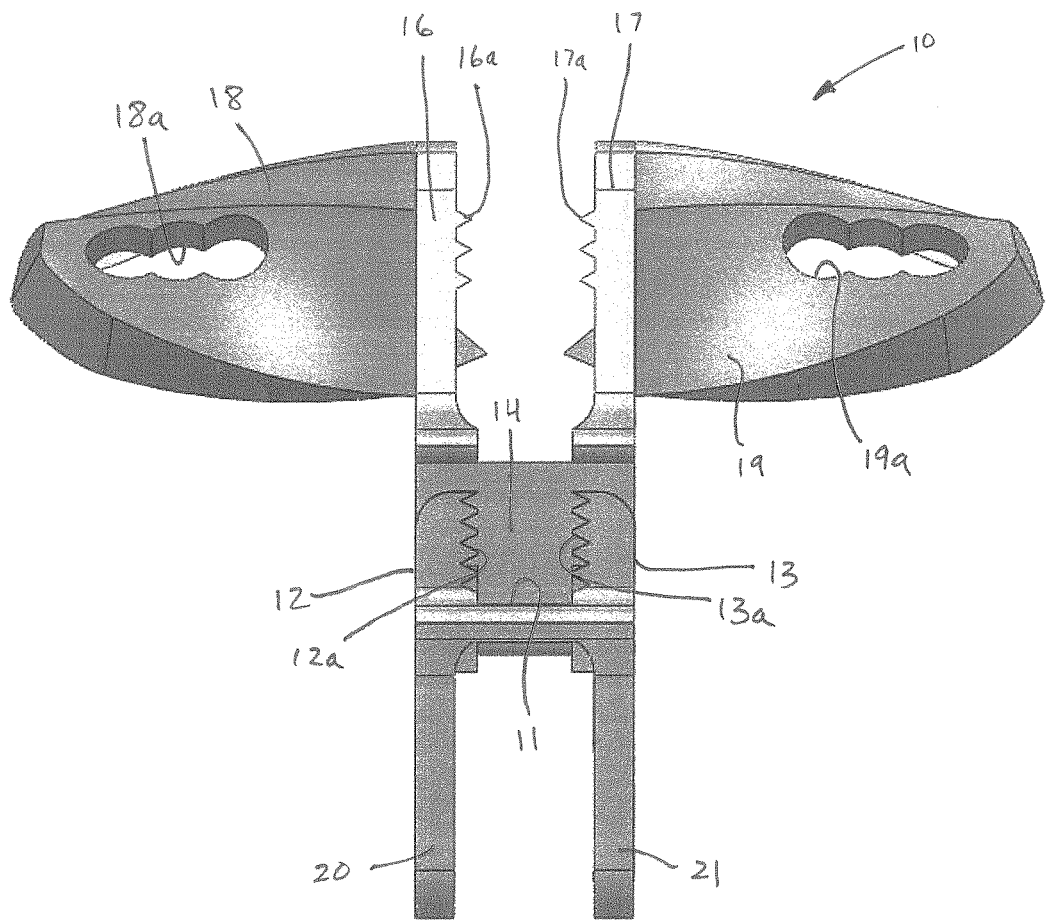
FIG. 2 is a front elevational view of the first embodiment of the interspinous fusion device illustrated in FIG. 1.
Figure 3:
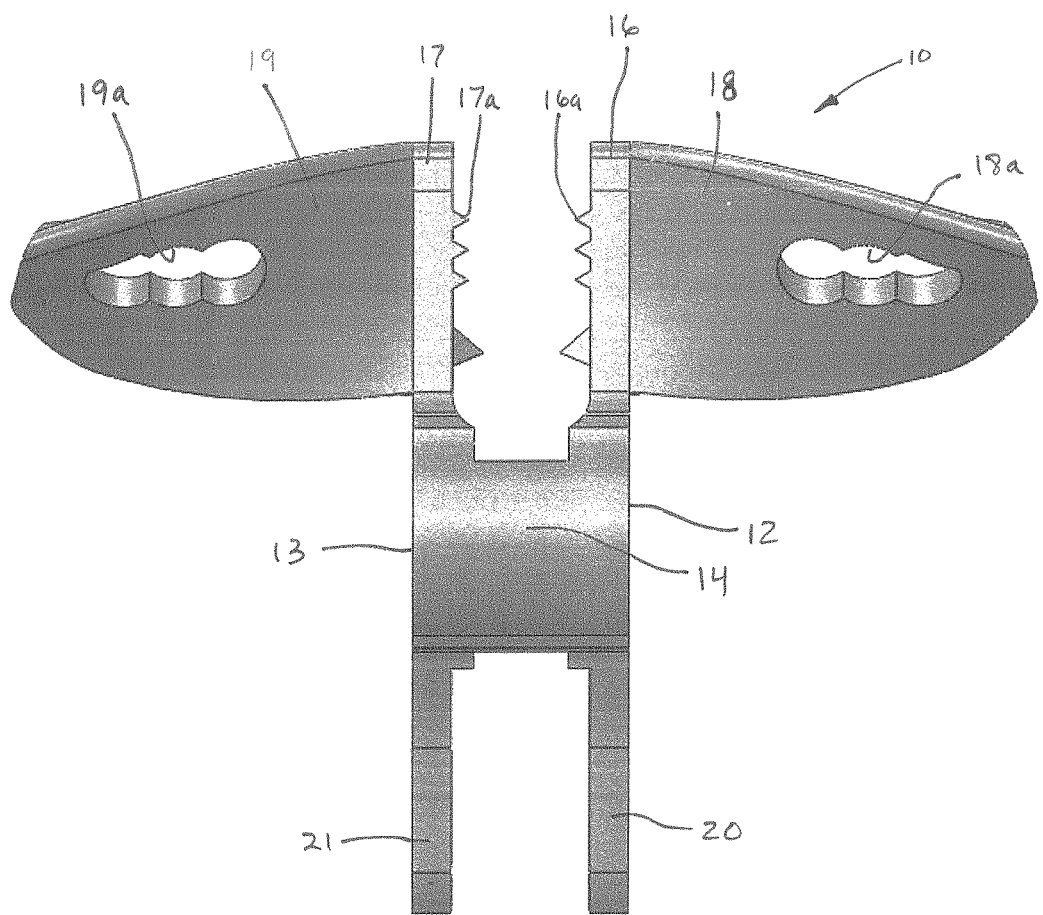
FIG. 3 is a rear elevational view of the first embodiment of the interspinous fusion device illustrated in FIGS. 1 and 2.

Referring now to the drawings, there is illustrated in FIGS. 1 through 4 a first embodiment of an interspinous fusion device, indicated generally at 10, in accordance with this invention. The interspinous fusion device 10 includes a central body portion that is defined by a bottom wall 11, first and second opposed side walls 12 and 13, and a rear wall 14. The bottom wall 11, the side walls 12 and 13, and the rear wall 14 cooperate to define a partially enclosed space, the purpose of which will be explained below. The side walls 12 and 13 have respective inwardly facing serrated surfaces 12a and 13a provided thereon. Also, the side walls 12 and 13 have respective apertures 12b and 13b formed therethrough. The purposes for these structures will also be explained below.

Figure 4:
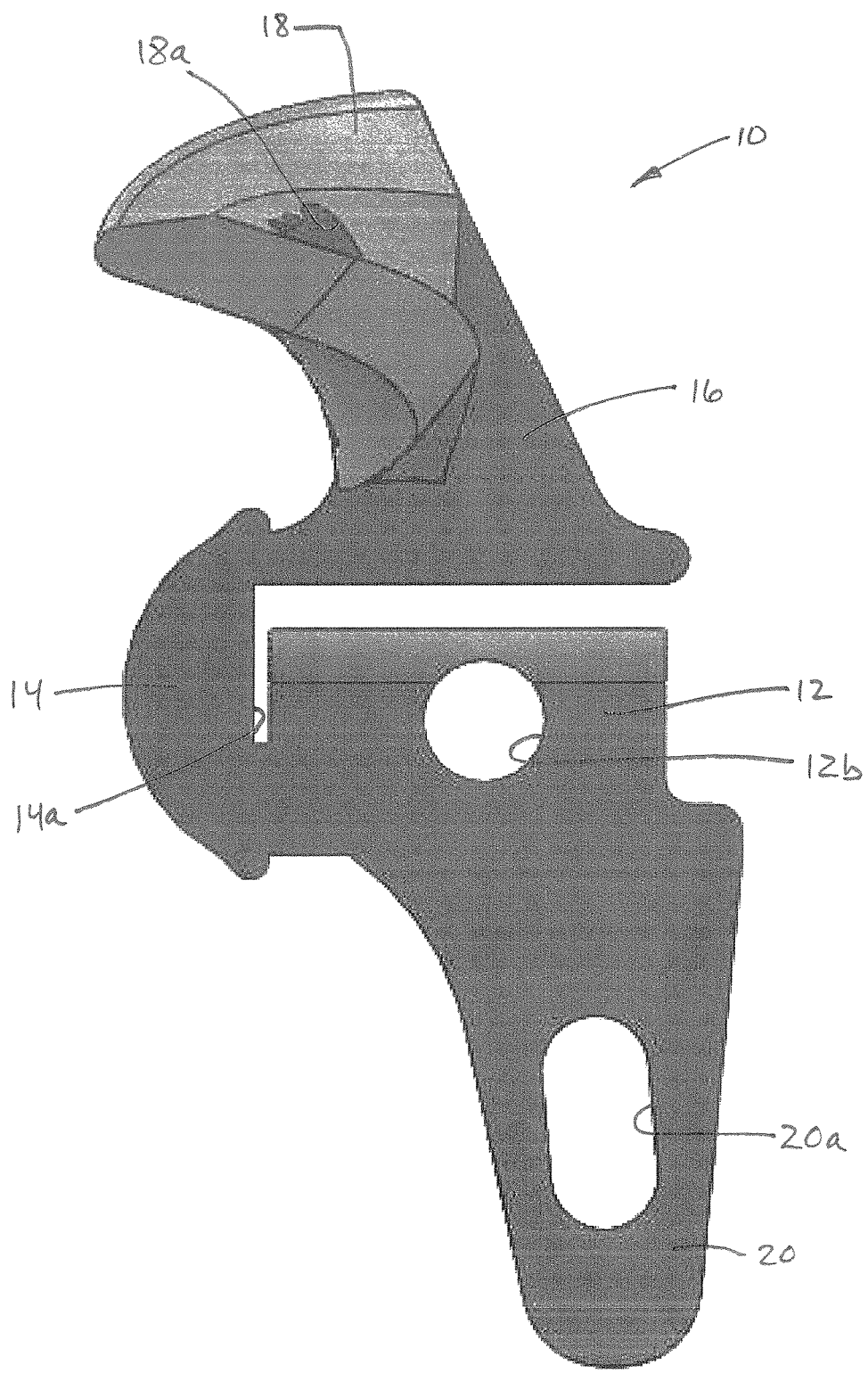
FIG. 4 is a side elevational view of the first embodiment of the interspinous fusion device illustrated in FIGS. 1 through 3.

As best shown in FIG. 4, a slot 14a is formed between portions of the side walls 12 and 13 and the rear wall 14 so as to define a spring-like hinge between the bottom wall 11 and the rear wall 14 of the interspinous fusion device 10. This spring-like hinge allows a limited amount of pivoting movement of the rear wall 14 relative to the bottom wall 11. The purpose for allowing this pivoting movement will be explained below.

First and second mounting plates 16 and 17 are respectively secured to the rear wall 14 of the interspinous fusion device 10, extending upwardly therefrom above the side walls 12 and 13, respectively. The mounting plates 16 and 17 have respective inwardly facing serrated surfaces 16a and 17a provided thereon, the purpose of which will be explained below. First and second mounting plates 18 and 19 are respectively secured to the upper ends of the first and second mounting plates 16 and 17. In the illustrated embodiment, the mounting plates 18 and 19 extend laterally outwardly in opposite directions from the upper ends of the mounting plates 16 and 17, although such is not required. Each of the illustrated mounting plates 18 and 19 is shaped having a torsional twist as it extends laterally outwardly from the associated brackets 16 and 17. However, the mounting plates 18 and 19 may have any desired shape or combination of shapes. Additionally, the mounting plates 18 and 19 need not be fixed in position relative to the associated brackets 16 and 17, but rather may be movable relative thereto in a poly-axial manner, as described below. In either event, the mounting plates 18 and 19 have respective apertures 18a and 19a formed therethrough for a purpose that will be explained below.

First and second connecting plates 20 and 21 are respectively secured to the lower ends of the first and second side walls 12 and 13 of the central body portion of the interspinous fusion device 10. In the illustrated embodiment, the connecting plates 20 and 21 are each generally planar and extend parallel to one another. However, the connecting plates 20 and 21 may have any desired shape or combination of shapes. The connecting plates 20 and 21 have respective slot-shaped apertures 20a and 21a formed therethrough. The purposes for the connecting plates 20 and 21 and the slot-shaped apertures 20a and 21a will be explained below.

The interspinous fusion device 10 is adapted to be secured to pair of adjacent vertebrae (not shown) in a spine to stabilize the relative positioning therebetween and to facilitate the placement of a bone-growth material, such as a bone graft material, to enhance bone growth and fusion of the adjacent vertebrae. To accomplish this, the first and second mounting plates 18 and 19 are adapted to be secured to an upper one of the pair of adjacent vertebrae. To accomplish this, the interspinous fusion device 10 is initially positioned such that the first and second mounting plates 18 and 19 are disposed adjacent to respective facets or other portions of the upper vertebra. Then, one or more fasteners (not shown), such as conventional bone screws, can be inserted through each of the apertures 18a and 19a into engagement with the adjacent facets or other portions of the upper vertebra. In this manner, the first and second mounting plates 18 and 19 of the interspinous fusion device 10 can be secured to the upper one of the pair of adjacent vertebrae.

As shown in the drawings, either or both of the apertures 18a and 19a formed through the first and second mounting plates 18 and 19 can be shaped to permit the fasteners to extend therethrough at multiple locations. In the illustrated embodiment, both of the apertures 18a and 19a are irregularly shaped so as to define plural discrete positions on the mounting plates 18 and 19 through which the fasteners may extend into engagement with the adjacent facets or other portions of the upper vertebra. These plural discrete positions provide desirable flexibility during the installation process, inasmuch as the geometries of each of the upper pair of adjacent vertebrae can vary in accordance with the specific anatomy of the patient. The interspinous fusion device 10 of this invention can readily accommodate such variations in anatomy because the fasteners can be provided at any selected one of the plural discrete positions defined by the apertures 18a and 19a that is deemed to be most appropriate based upon such anatomy.

Additionally, as discussed above, the illustrated mounting plates 18 and 19 extend laterally outwardly in opposite directions from the upper ends of the side walls 12 and 13, and each is shaped having a torsional twist. The shapes of the first and second mounting plates 18 and 19 are such that relatively large surface areas thereof engage the respective facets or other portions of the upper vertebra. Such relatively large surface area engagement functions to distribute load forces imparted by the interspinous fusion device 10 more evenly across the surface areas of the respective facets or other portions of the upper vertebra. As a result, the generation of undesirable localized stresses on the facets or other portions of the upper vertebra is substantially reduced or avoided.

The first and second connecting plates 20 and 21 of the interspinous fusion device are adapted to be secured to a lower one of the pair of adjacent vertebrae. To accomplish this, the interspinous fusion device 10 is initially positioned such that the first and second connecting plates 20 and 21 are disposed about a spinous process or other portion of the lower vertebra. Then, one or more fasteners (not shown), such as conventional bone screws, can be inserted through each of the slot-shaped apertures 20a and 21a of the connecting plates 20 and 21 and through the spinous process or other portion of the lower vertebra. In this manner, the first and second connecting plates 20 and 21 of the interspinous fusion device 10 can be secured to the lower one of the pair of adjacent vertebrae.

As mentioned above, the bottom wall 11, the side walls 12 and 13, and the rear wall 14 cooperate to define a partially enclosed space within the interspinous fusion device 10. This partially enclosed space can be used to receive a quantity of a bone-growth material, such as a bone graft material, to enhance bone growth and fusion of the adjacent vertebrae. The partially enclosed space within the interspinous fusion device further functions to prevent the bone-growth material from undesirably flowing out of the region between the adjacent vertebrae. The inwardly facing serrated surfaces 12a and 13a and the apertures 12b and 13b on the side walls 12 and 13 provide irregularly shaped surfaces that are well adapted to be engaged by the bone-growth material, thereby functioning to positively retain such material within the central body portion of the interspinous fusion device 10. The mounting inwardly facing serrated surfaces 16a and 17a of the mounting plates 16 and 17 function in the same manner.

As also mentioned above, the interspinous stabilization device 10 of this invention not only more evenly distributes loads throughout the adjacent vertebrae than known interspinous stabilization devices, but also can readily compensate for graft settling so as to maintain continued axial loading of the graft material disposed between the adjacent vertebrae. In the interspinous stabilization device 10 of this invention, this is accomplished by the provision of the two slot-shaped apertures 20a and 21a formed through the connecting plates 20 and 21. During the above-described installation process, the first and second connecting plates 20 and 21 are disposed about a spinous process or other portion of the lower vertebra, and a fastener is inserted through the slot-shaped apertures 20a and 21a and through the spinous process of the lower vertebra. As settling of the bone graft material occurs, the fastener can slide through the slot-shaped apertures 20a and 21a, thereby allowing the distance between the two adjacent vertebrae to decrease as settling of the bone graft occurs. Consequently, the axial pressure exerted by such adjacent vertebrae on the bone graft material is effectively maintained as settling of the bone graft material occurs.

Additionally, as also described above, the slot 14a formed between portions of the side walls 12 and 13 and the rear wall 14 defines a spring-like hinge between the bottom wall 11 and the rear wall 14 of the interspinous fusion device 10. This spring-like hinge allows a limited amount of pivoting movement of the rear wall 14 relative to the bottom wall 11. As a result, the axial pressure exerted by such adjacent vertebrae on the bone graft material is effectively maintained as settling of the bone graft material occurs.

Thus, the dynamic system of this invention is designed to take full advantage of Wolff's law of dynamic osteosynthesis. By avoiding stress shielding and allowing full load sharing, earlier and more substantial graft incorporation can occur. The unique slot-shaped apertures 20a and 21a and slot 14a are designed to compensate for graft setting (bone graft or special scaffold material, such as calcium phosphate, etc.) so as to maintain continued axial loading on the graft. Axial settling, which allows full load sharing capability, occurs because the fasteners are free to move through the slot-shaped apertures 20a and 21 formed through the first and second connecting plates 20 and 21 and because the spring-like hinge defined between the bottom wall 11 and the rear wall 14 of the interspinous fusion device 10 allows a limited amount of pivoting movement of the mounting plates 16 and 17 (which are connected to the upper vertebra) relative to the connecting plates 20 and 21 (which are connected to the lower vertebra). As a result, the amount of this settling distance is determined by the amount of graft resorption, not because of any physical restriction imposed by the interspinous stabilization device 10 of this invention. Also, compression of the bone graft material as explained above is facilitated.

Figure 5A:
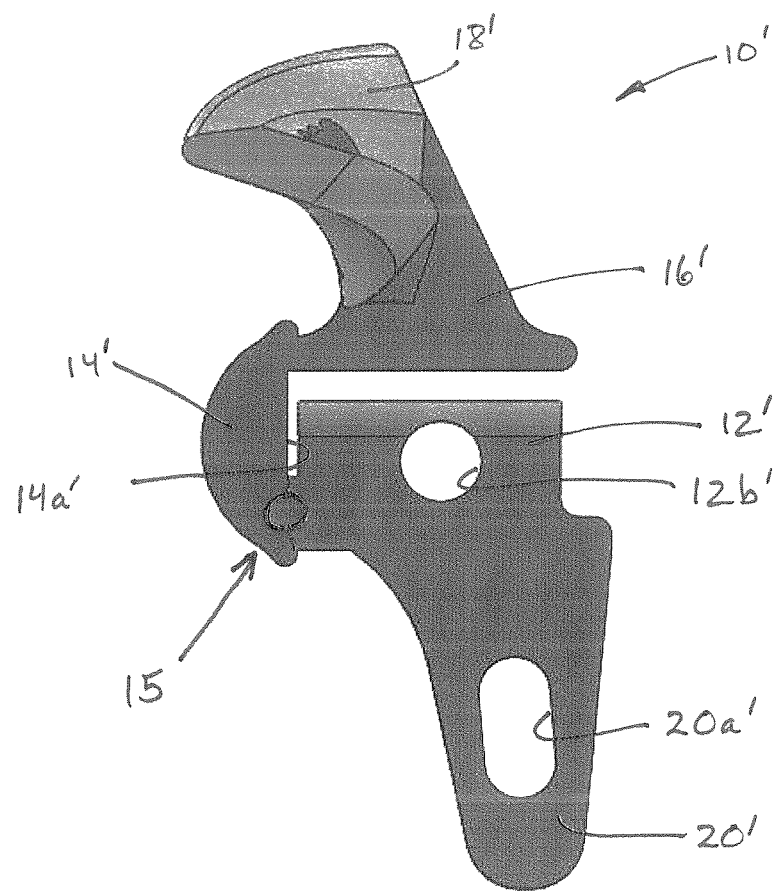
FIG. 5A is a side elevational view of a modified version of the first embodiment of the interspinous fusion device illustrated in FIG. 4.
Figure 5B:
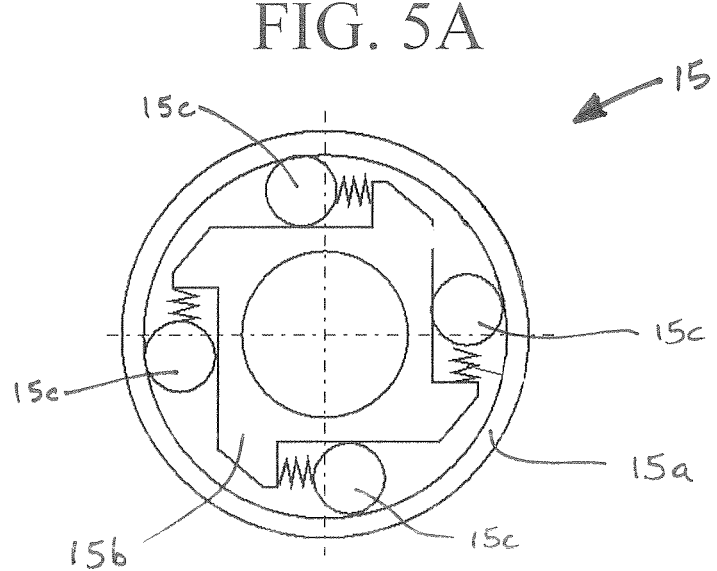
FIG. 5B is a schematic view of a movement-limiting mechanism that can be used with the modified version of the first embodiment of the interspinous fusion device illustrated in FIG. 5A.

Referring now to FIGS. 5A and 5B, there is illustrated a modified version 10' of the first embodiment of the interspinous fusion device illustrated in FIGS. 1 through 4, wherein like reference numbers are used to identify similar structures. In this modified version 10', a movement-limiting mechanism, indicated generally at 15, is provided with (or in lieu of) the spring-like hinge to limit the pivoting movement of the mounting plates 16 and 17 relative to the connecting plates 20 and 21 to a single rotational direction. An exemplary structure of the movement-limiting mechanism 15 is illustrated in FIG. 5B. As shown therein, the movement-limiting mechanism 15 can include an outer ring 15a that is secured to one of the bottom wall 11 and the rear wall 14, an inner hub 15b that is secured to the other of the bottom wall 11 and the rear wall 14, and one or more spring-loaded balls 15c disposed between the outer ring 15a and the inner hub 15b. The spring-loaded balls 15c cooperate with the outer ring 15a and the inner hub 15b in a manner that is well known in the art to allow relative movement to occur only in one rotation direction. As a result, the movement-limiting mechanism 15 may be used to restrict the pivoting movement of the rear wall 14 relative to the bottom wall 11 to allow extension of the joint between the adjacent vertebrae but not flexion. It will be appreciated that the movement-limiting mechanism 15 may also be used in connection with any of the embodiments described herein.

Referring now to FIGS. 6 through 11, there is illustrated a second embodiment of an interspinous fusion device, indicated generally at 110, in accordance with this invention.

The second embodiment of the interspinous fusion device 110 is similar to the first embodiment of the interspinous fusion device 10 described above, and like reference numbers (incremented by 100) are used to indicate similar structures. In this second embodiment of the interspinous fusion device 110, however, the mounting plates 118 and 119 (see FIGS. 10 and 11) are not fixed in position relative to the upper ends of the first and second mounting plates 116 and 117. Rather, the mounting plates 118 and 119 are respectively secured to the upper ends of the first and second mounting plates 116 and 117 in a manner that allows for poly-axial or other relative movement.

Figure 10:
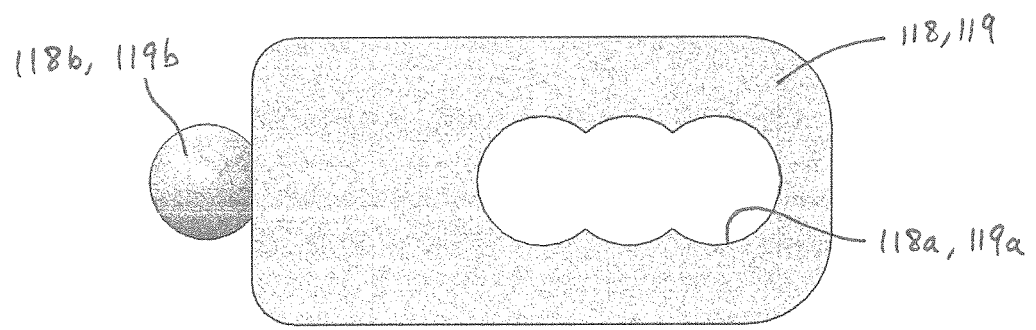
FIG. 10 is an enlarged front elevational view of a poly-axial mounting plate that can be used with the second embodiment of the interspinous fusion device illustrated in FIGS. 6 through 9.
Figure 11:
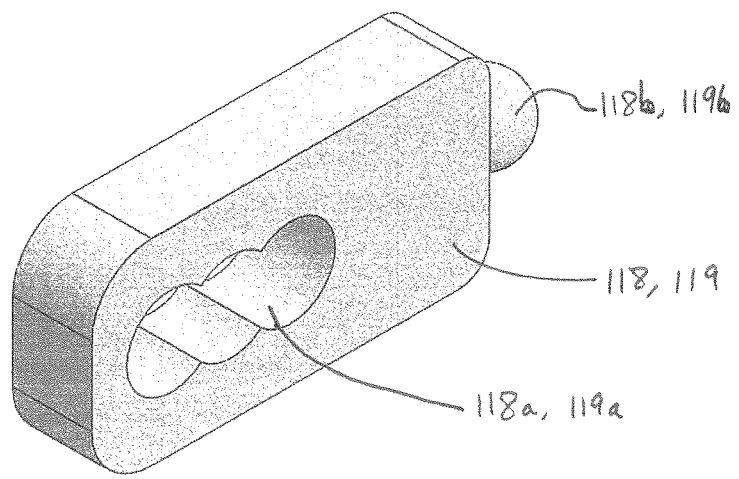
FIG. 11 is a perspective view of the poly-axial mounting plate illustrated in FIG. 10.

In the illustrated embodiment, this is accomplished by providing each of mounting plates 116 and 117 with a mounting structure 116b and 117b, and further by providing each of the mounting plates 118 and 119 with a cooperating mounting structure 118a and 119a. As shown in FIGS. 6 through 9, the illustrated mounting structures 116b and 117b are generally hollow and cylindrical in shape and extend laterally outwardly in opposite directions from the associated mounting plates 116 and 117. Each of the hollow cylindrical mounting structures 116b and 117b has an outer surface, an inner surface, and a transverse aperture that extends from the outer surface to the inner surface. As shown in FIGS. 10 and 11, the illustrated mounting structures 118a and 119a of the mounting plates 118 and 119 are generally spherical in shape. The spherical mounting structures 118a and 119a of the mounting plates 118 and 119 are sized and shaped to fit snugly within the hollow cylindrical mounting structures 116b and 117b of the mounting plates 116 and 117. As a result, the positions of the mounting plates 118 and 119 relative to the associated mounting plates 116 and 117 can be adjusted in a poly-axial manner to correspond with the anatomy of the vertebra to which they are secured, as described above. When a desired relative positioning has been achieved, the mounting plates 118 and 119 can be locked in those relative positions by set screws (not shown) that extend respectively through each of the transverse apertures formed through the hollow cylindrical mounting structures 116b and 117b of the mounting plates 116 and 117 into engagement with the spherical mounting structures 118a and 119a of the mounting plates 118 and 119. However, the mounting plates 118 and 119 can be locked in those relative positions by any desired means.

Figures 6, 7:
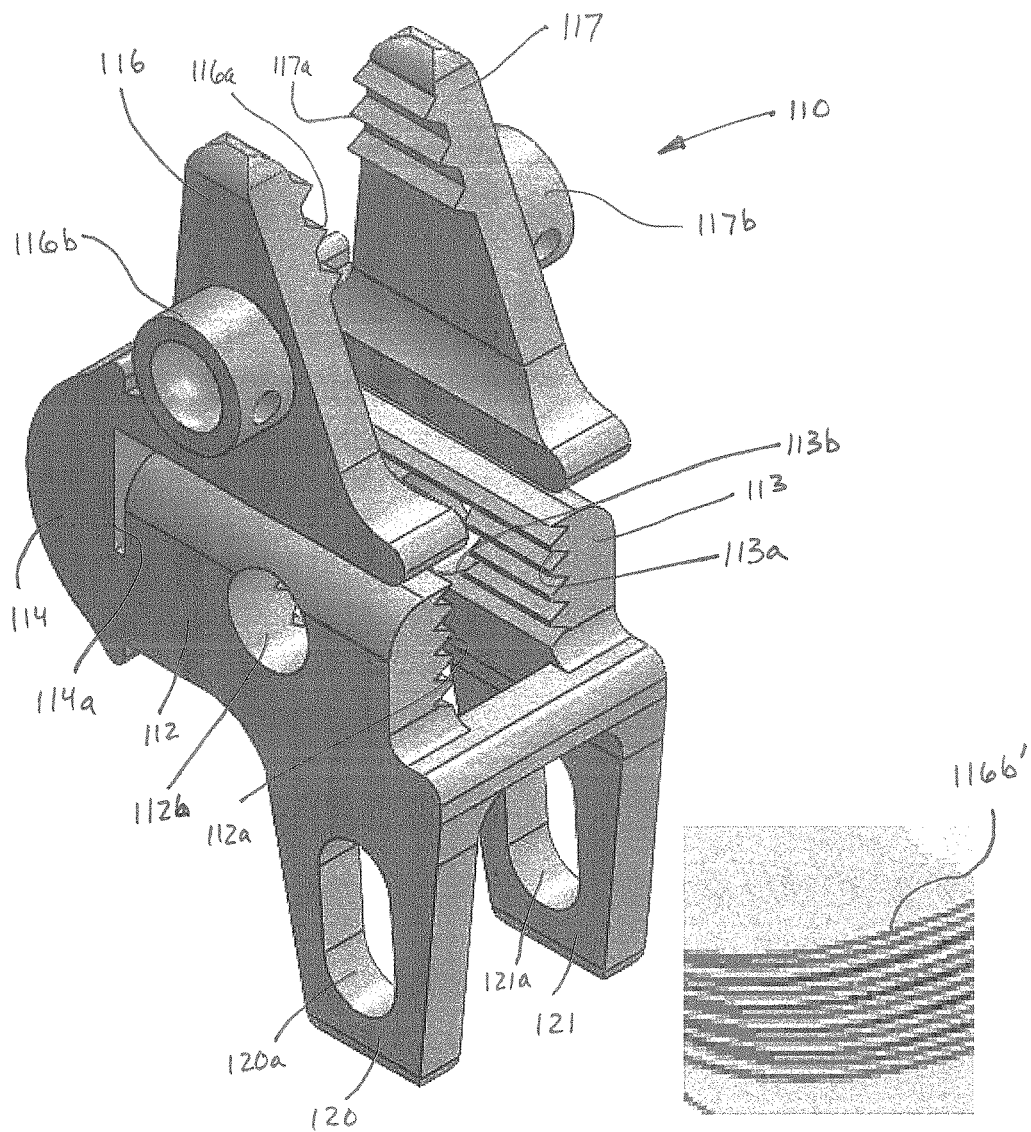
FIG. 6 is a perspective view of a portion of a second embodiment of an interspinous fusion device in accordance with this invention.
FIG. 7 is an enlarged view of a portion of the second embodiment of the interspinous fusion device illustrated in FIG. 6.
Figure 8:
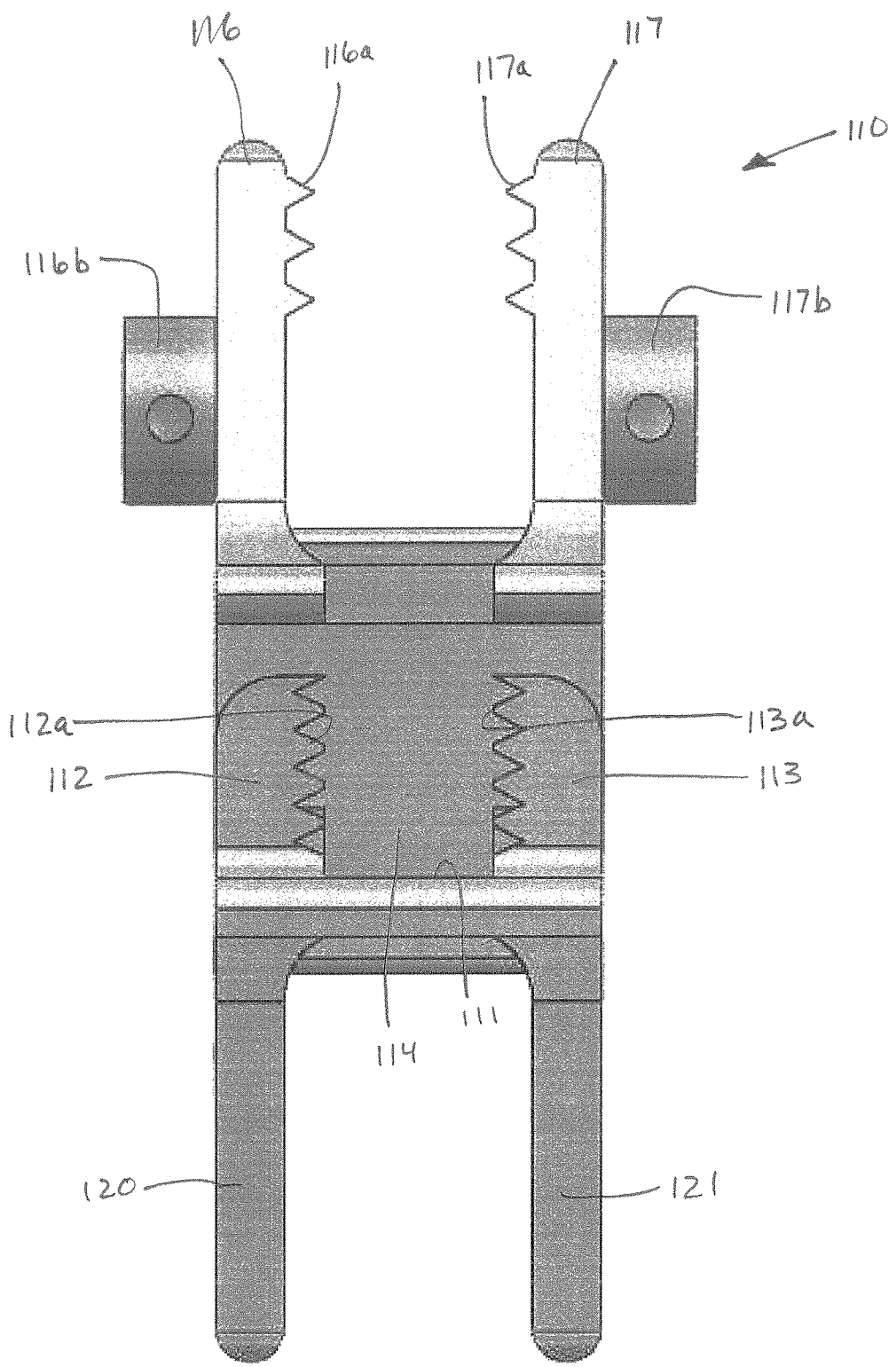
FIG. 8 is a front elevational view of the second embodiment of the interspinous fusion device illustrated in FIGS. 6 and 7.
Figure 9:
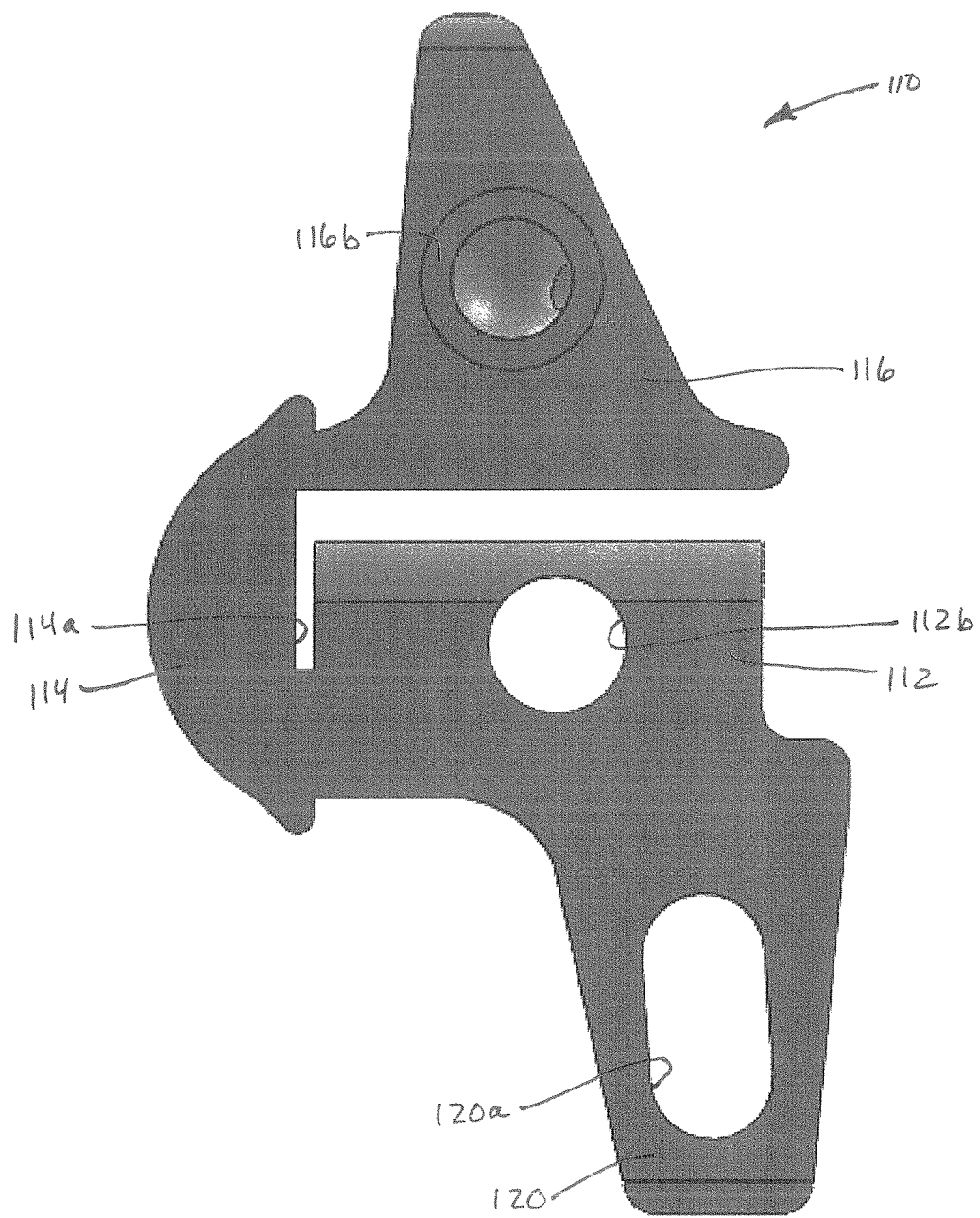
FIG. 9 is a side elevational view of the second embodiment of the interspinous fusion device illustrated in FIGS. 6 through 8.
Figure 12:
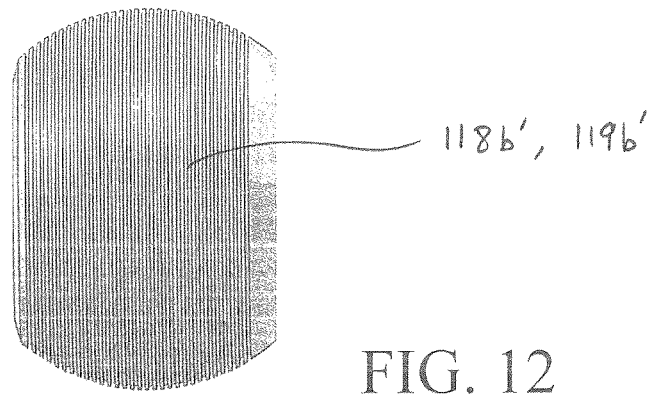
FIG. 12 is a further enlarged front elevational view of a modified portion of the poly-axial mounting plate illustrated in FIGS. 10 and 11.

As shown in FIG. 6, the inner surfaces of the hollow cylindrical mounting structures 116b and 117b of the mounting plates 116 and 117 are smooth. However, if desired, such inner surfaces of the hollow cylindrical mounting structures 116b and 117b may be formed having a serrated or other irregular shape, such as shown at 116b' in FIG. 7. Such irregular shape can provide an enhanced locking capability over smooth inner surface. Similarly, as shown in FIGS. 10 and 11, the outer surfaces of the spherical mounting structures 118a and 119a of the mounting plates 118 and 119 are smooth. However, if desired, such outer surfaces of the spherical mounting structures may be formed having a serrated or other irregular shape, such as shown at 118a' and 119a' in FIG. 12. Such irregular shape can similarly provide an enhanced locking capability over smooth outer surface. Either or both of the inner surfaces of the hollow cylindrical mounting structures 116b and 117b and the outer surfaces of the spherical mounting structures 118a and 119a may be formed in this manner.

FIGS. 13 through 18 are perspective views of alternative embodiments of one of the poly-axial mounting plates 118 illustrated in FIGS. 9 through 12.

Figure 13:
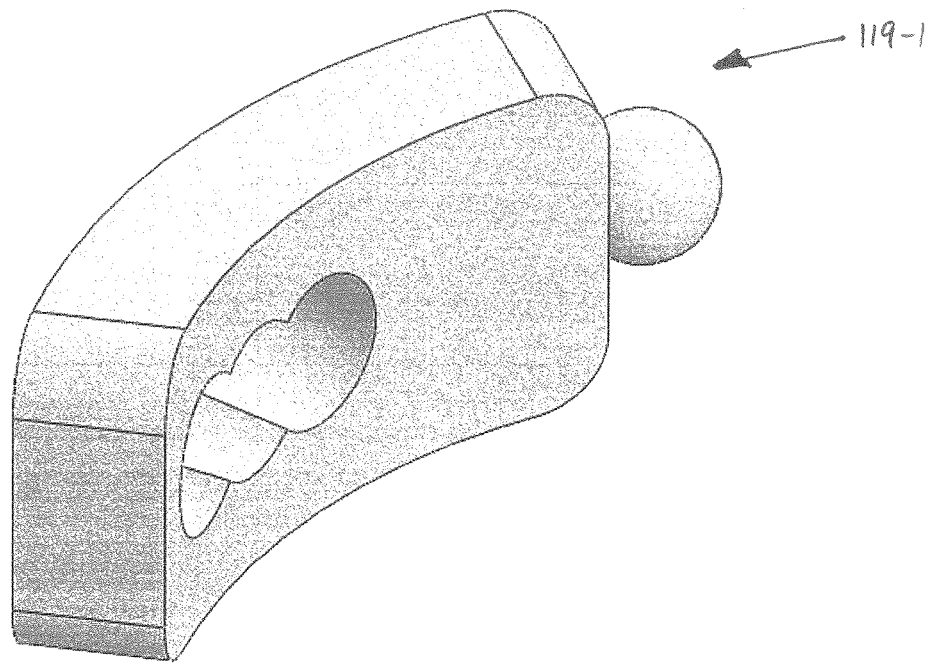
FIGS. 13 through 18 are perspective views of alternative embodiments of the poly-axial mounting plate illustrated in FIGS. 9 through 12.
Figure 14:
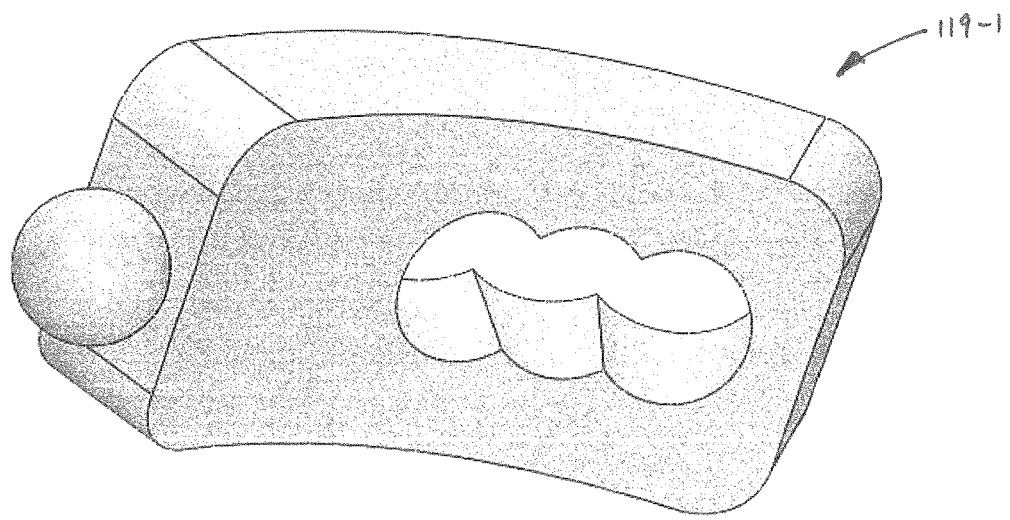
Figures 15, 16:
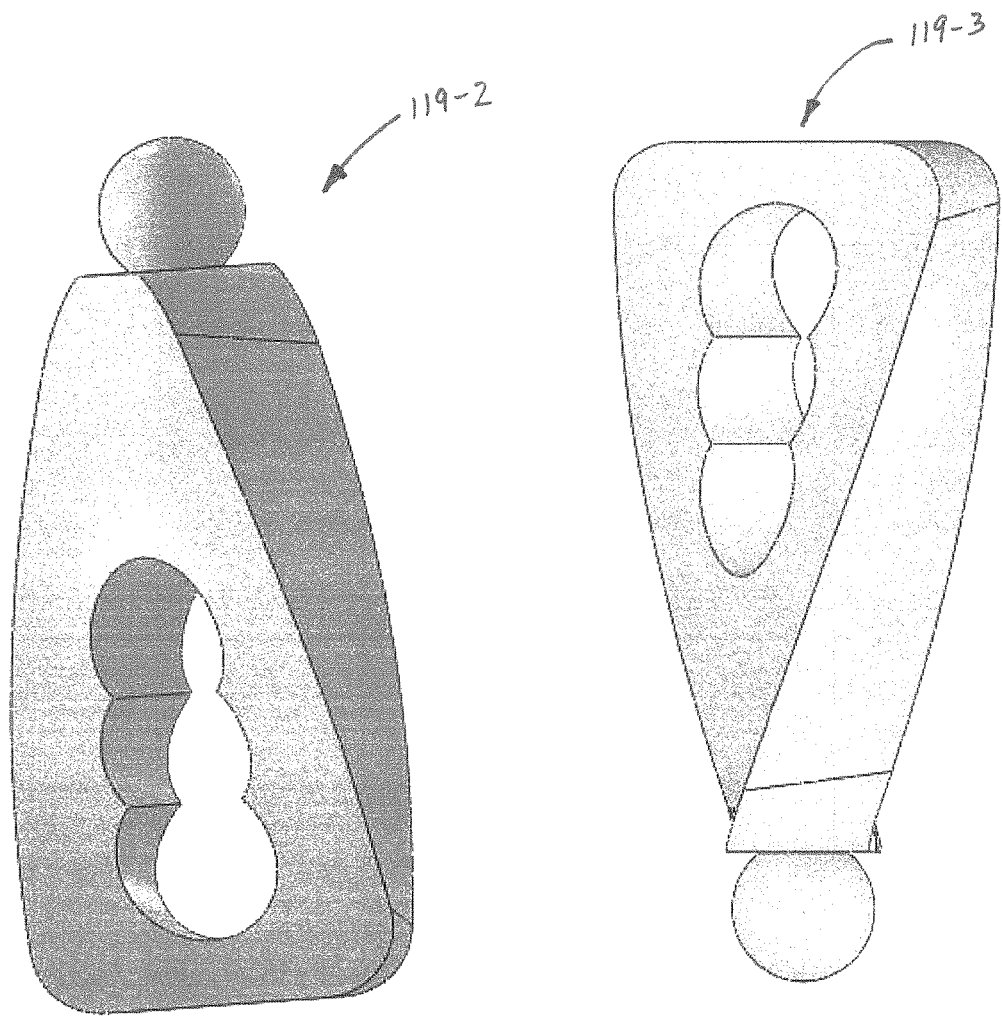
Figure 17:
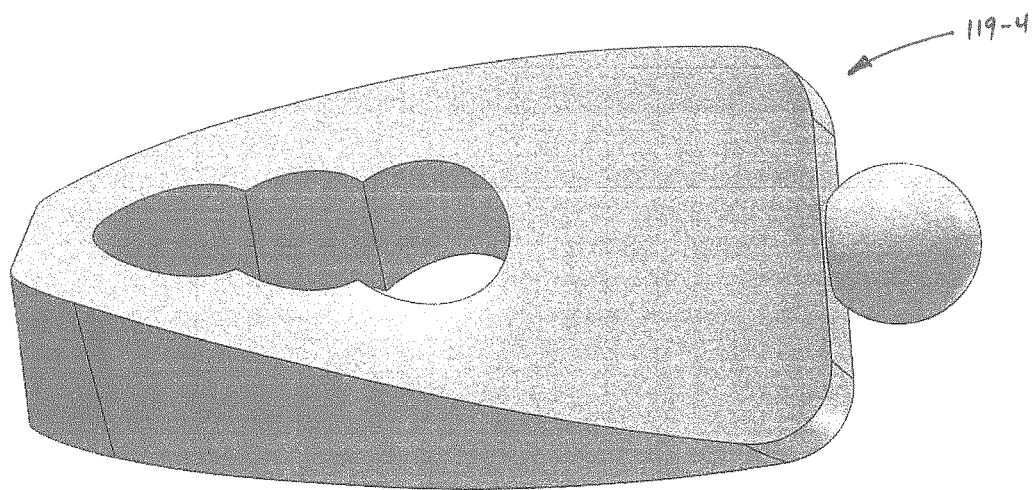
Figure 18:
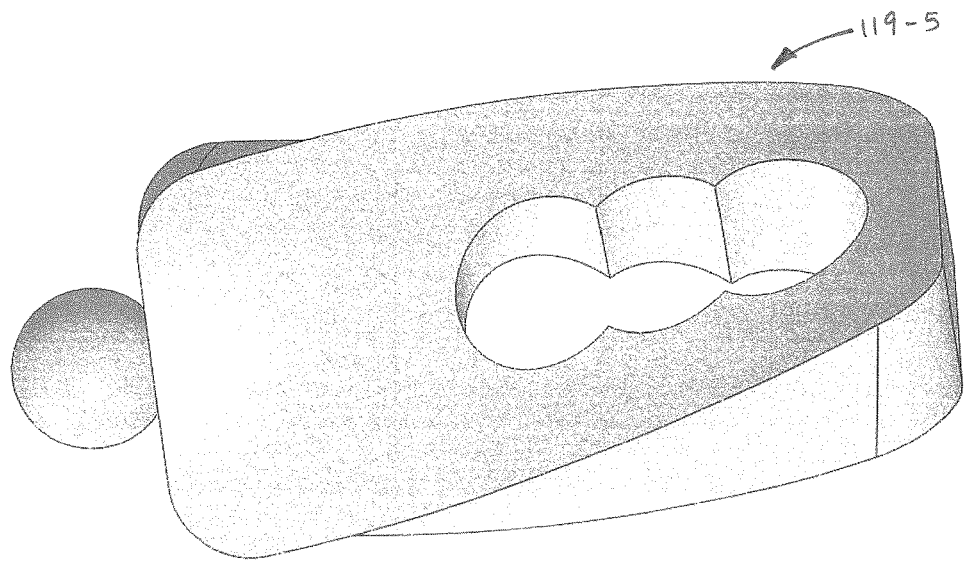

In FIGS. 13 and 14, a first modified mounting plate 119-1 is curved from end to end, has a generally uniform thickness throughout, and has a generally uniform width throughout. In FIG. 15, a second modified mounting plate 119-2 is linear from end to end, has a thickness that varies from a relatively thick portion adjacent to the mounting structure to a relatively thin portion adjacent an outer end thereof, and has a width that varies from a relatively narrow portion adjacent to the mounting structure to a relatively wide portion adjacent the outer end thereof. In FIG. 16, a third modified mounting plate 119-3 has a torsional twist from end to end, has a generally uniform thickness throughout, and has a width that varies from a relatively narrow portion adjacent to the mounting structure to a relatively wide portion adjacent an outer end thereof. In FIG. 17, a fourth modified mounting plate 119-4 is linear from end to end, has a thickness that varies from a relatively thin portion adjacent to the mounting structure to a relatively thick portion adjacent an outer end thereof, and has a width that is generally uniform throughout. Lastly, in FIG. 18, a fifth modified mounting plate 119-5 is shaped having a torsional twist from end to end, has a generally uniform thickness throughout, and has a generally uniform width throughout.

Figure 19:
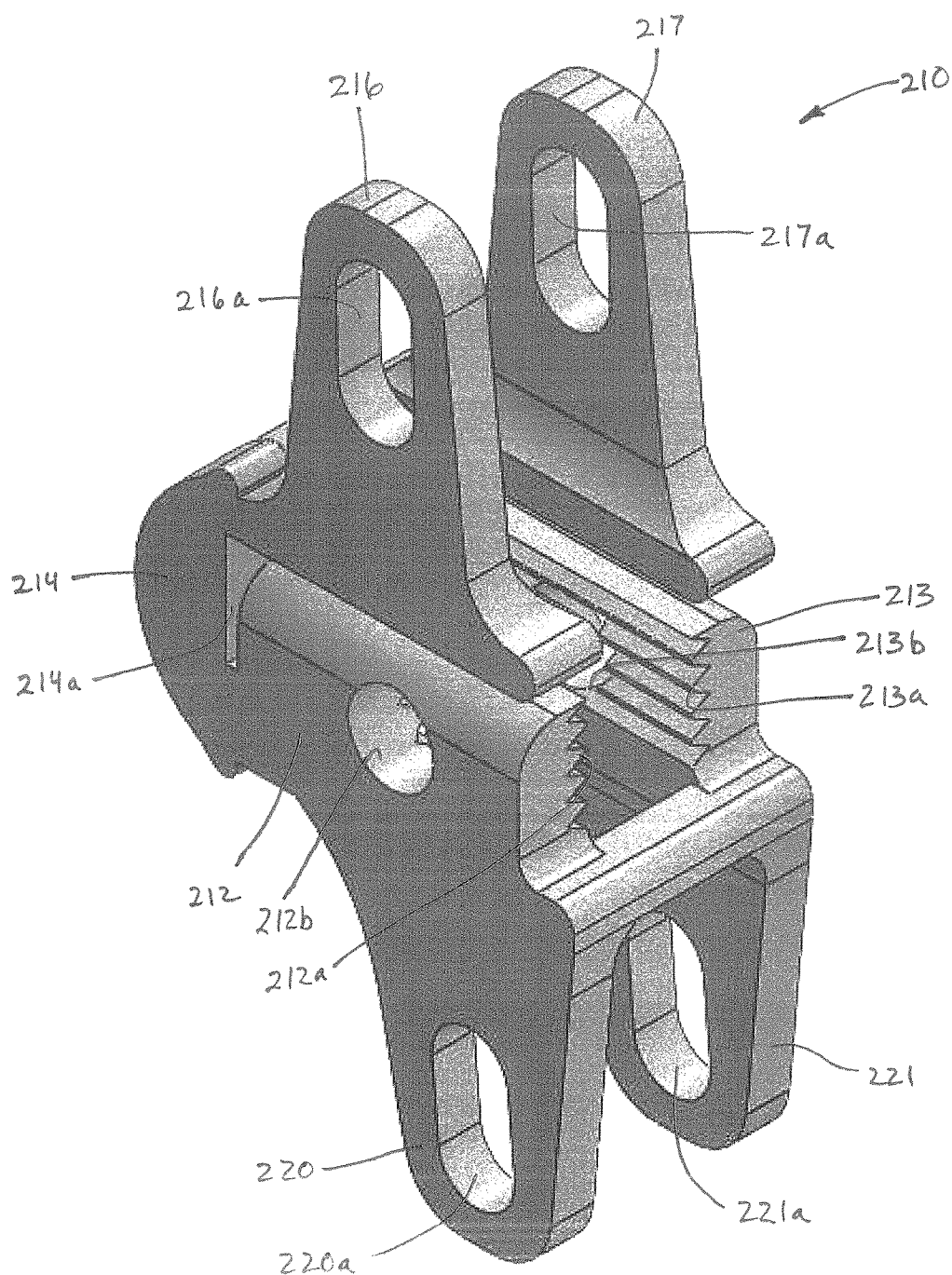
FIG. 19 is a perspective view of a third embodiment of an interspinous fusion device in accordance with this invention.
Figure 20:
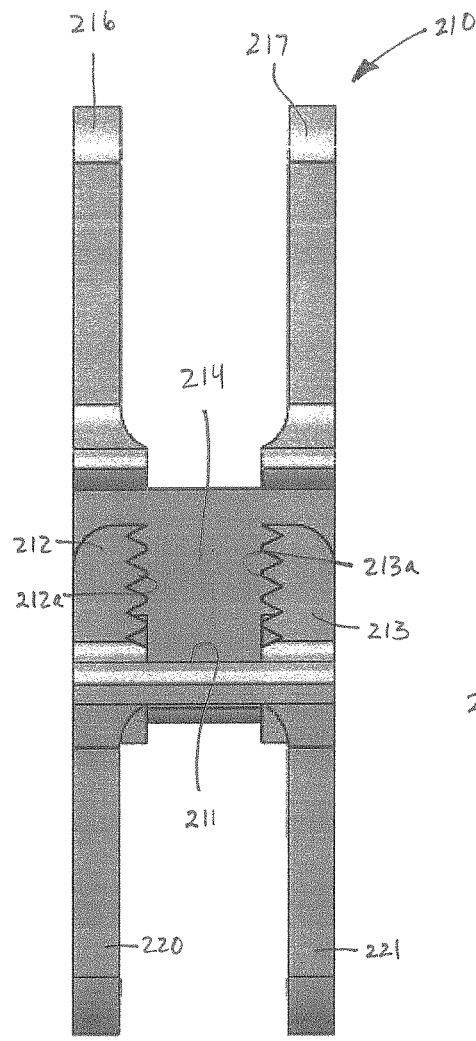
FIG. 20 is a front elevational view of the third embodiment of the interspinous fusion device illustrated in FIG. 19.
Figure 21:
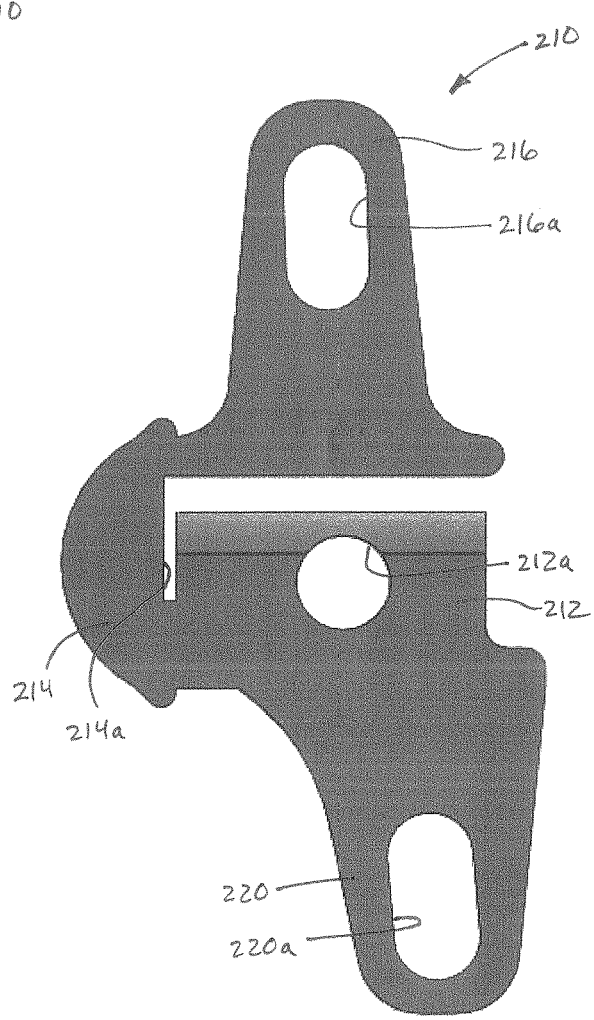
FIG. 21 is a side elevational view of the third embodiment of the interspinous fusion device illustrated in FIGS. 19 and 20.

Referring now to FIGS. 19 through 21, there is illustrated a third embodiment of an interspinous fusion device, indicated generally at 210, in accordance with this invention. The third embodiment of the interspinous fusion device 210 is similar to the first embodiment of the interspinous fusion device 10 described above, and like reference numbers (incremented by 200) are used to indicate similar structures. In this third embodiment of the interspinous fusion device 210, however, the mounting plates 216 and 217 have respective slot-shaped apertures 216a and 217a formed therethrough, and the mounting plates 18 and 19 are eliminated. In this embodiment, rather, the mounting plates 216 and 217 are secured directly to respective portions of the upper vertebra in a manner that is similar to how the connecting plates 20 and 21 are secured directly to respective portions of the lower vertebra, as described above. The slot-shaped apertures 216a and 217a function in a manner that is similar to the slot-shaped apertures 20a and 21a to maintain the axial pressure exerted by the adjacent vertebrae on the bone graft as settling of the bone graft material occurs.

Figure 22:
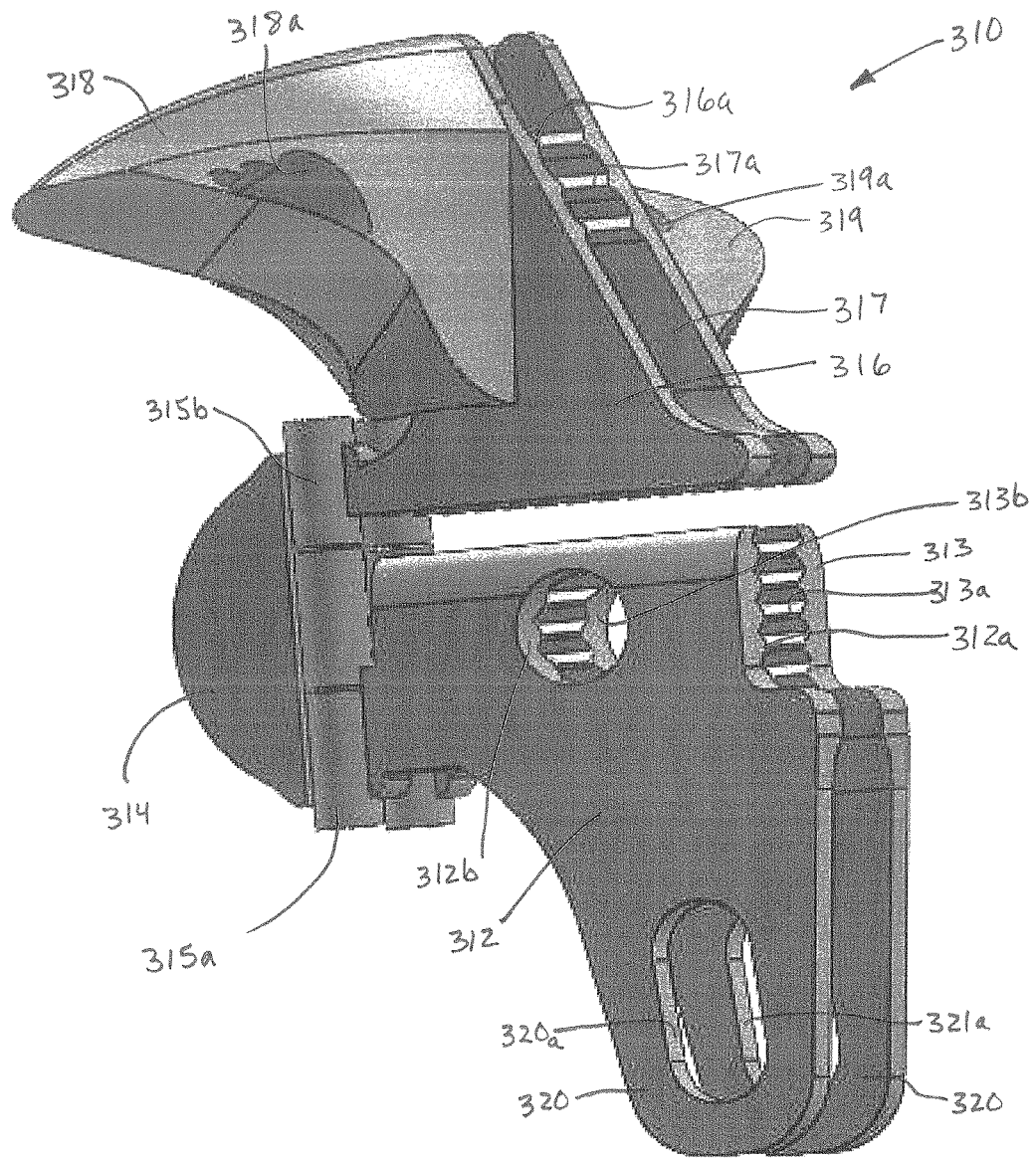
FIG. 22 is a perspective view of a fourth embodiment of an interspinous fusion device in accordance with this invention.
Figure 23:
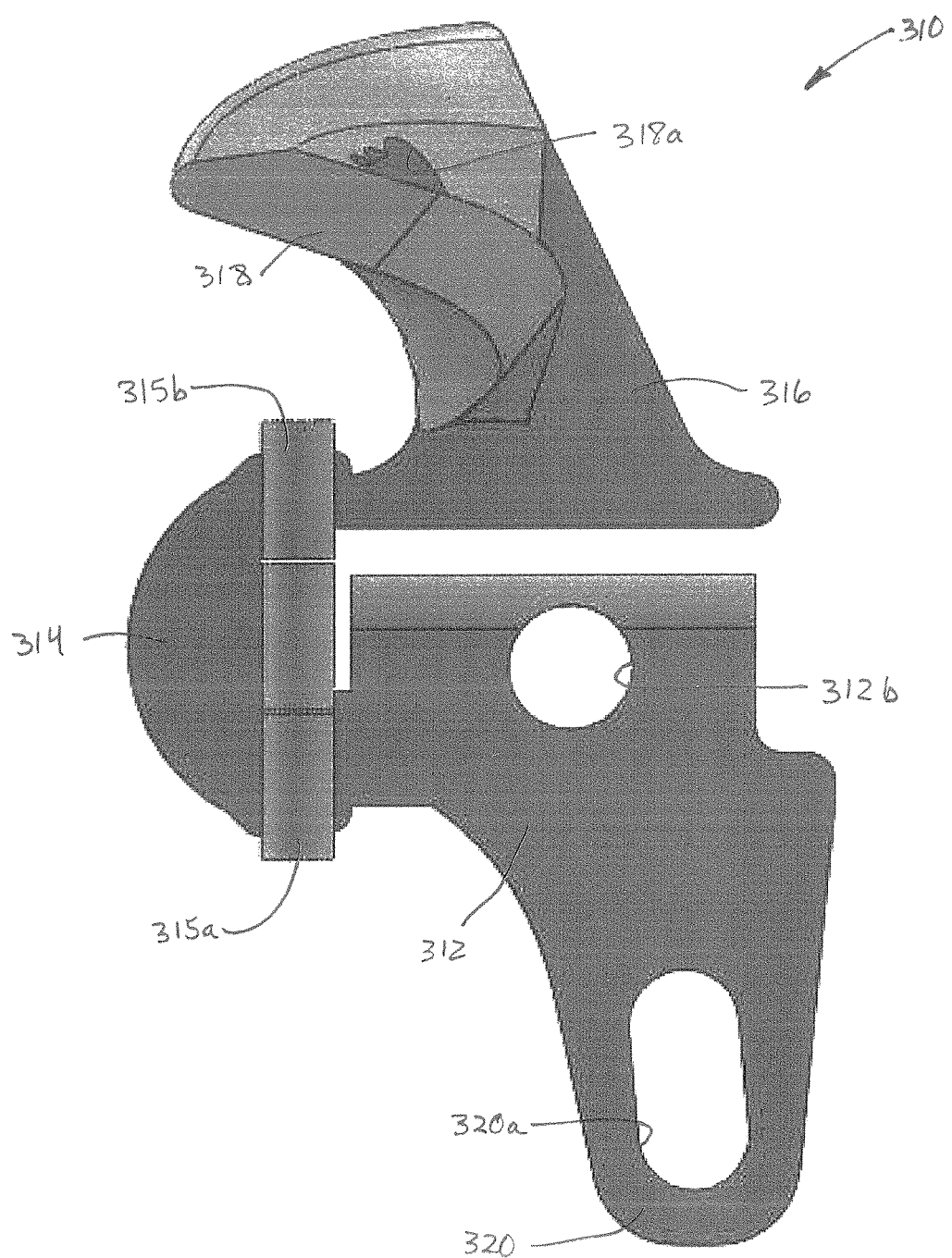
FIG. 23 is a side elevational view of the fourth embodiment of the interspinous fusion device illustrated in FIG. 22.
Figure 24:
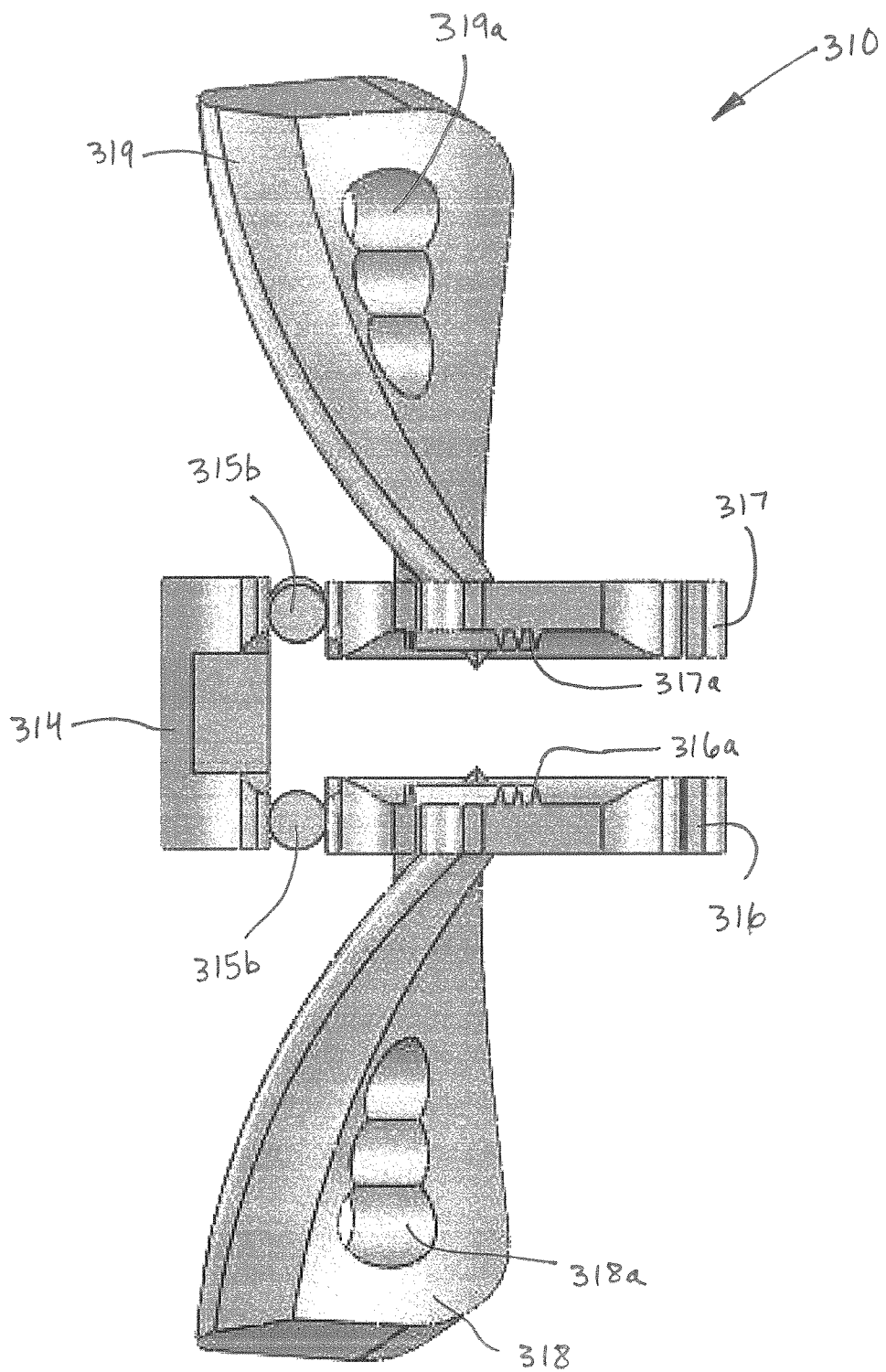
FIG. 24 is a top plan view of the fourth embodiment of the interspinous fusion device illustrated in FIGS. 22 and 23.

Referring now to FIGS. 22 through 24, there is illustrated a fourth embodiment of an interspinous fusion device, indicated generally at 310, in accordance with this invention. The fourth embodiment of the interspinous fusion device 310 is similar to the first embodiment of the interspinous fusion device 10 described above, and like reference numbers (incremented by 300) are used to indicate similar structures. In this fourth embodiment of the interspinous fusion device 310, however, the side walls 312 and 313 are connected to the back wall 314 by respective first hinges 315a. Thus, the side walls 312 and 313 can be pivoted inwardly and outwardly relative to one another and relative to the back wall 314 as desired. Similarly, the mounting plates 316 and 317 are connected to the back wall 314 by respective second hinges 315b. Thus, the mounting plates 316 and 317 can be pivoted inwardly and outwardly relative to one another and relative to the back wall 314 as desired. Consequently, the interspinous fusion device 310 can readily accommodate variations in the anatomy of the vertebrae to which the interspinous fusion device 310 is attached, as described above.

Figure 25:
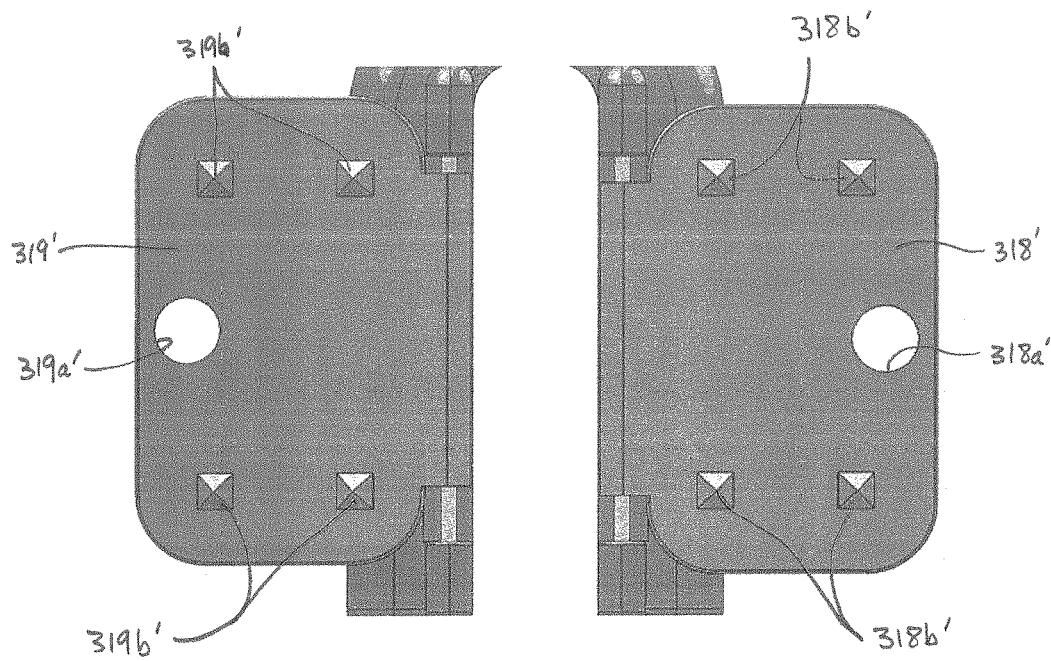
FIGS. 25 and 26 are rear elevational views of modified versions of the pivotable mounting plates illustrated in FIGS. 22 through 24.
Figure 26:
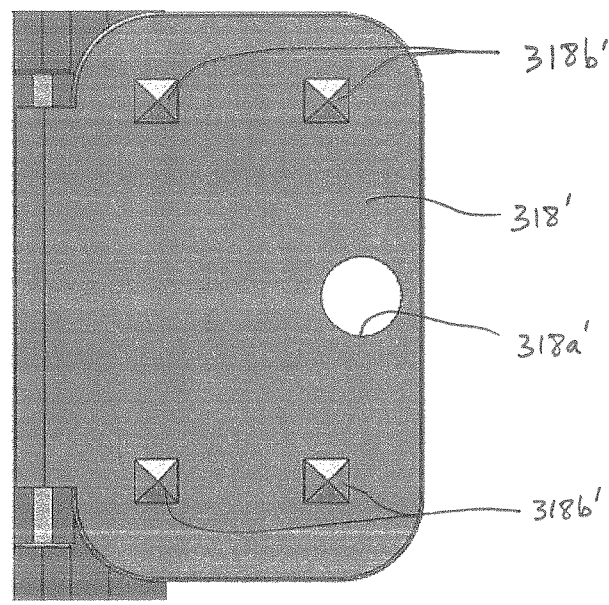

FIGS. 25 and 26 are rear elevational views of alternative embodiments of the pivotable mounting plates 318' and 319' illustrated in FIGS. 22 through 24. In addition to the apertures 318a' and 319a' formed respectively therethrough, each of the mounting plates 318' and 319' has one or more protrusions 318b' and 319b' formed thereon. The protrusions 318b' and 319b' are adapted to engage respective portions of the associated vertebra to provide a more positive locking engagement therewith and to more evenly distributes loads throughout.

Figure 27:
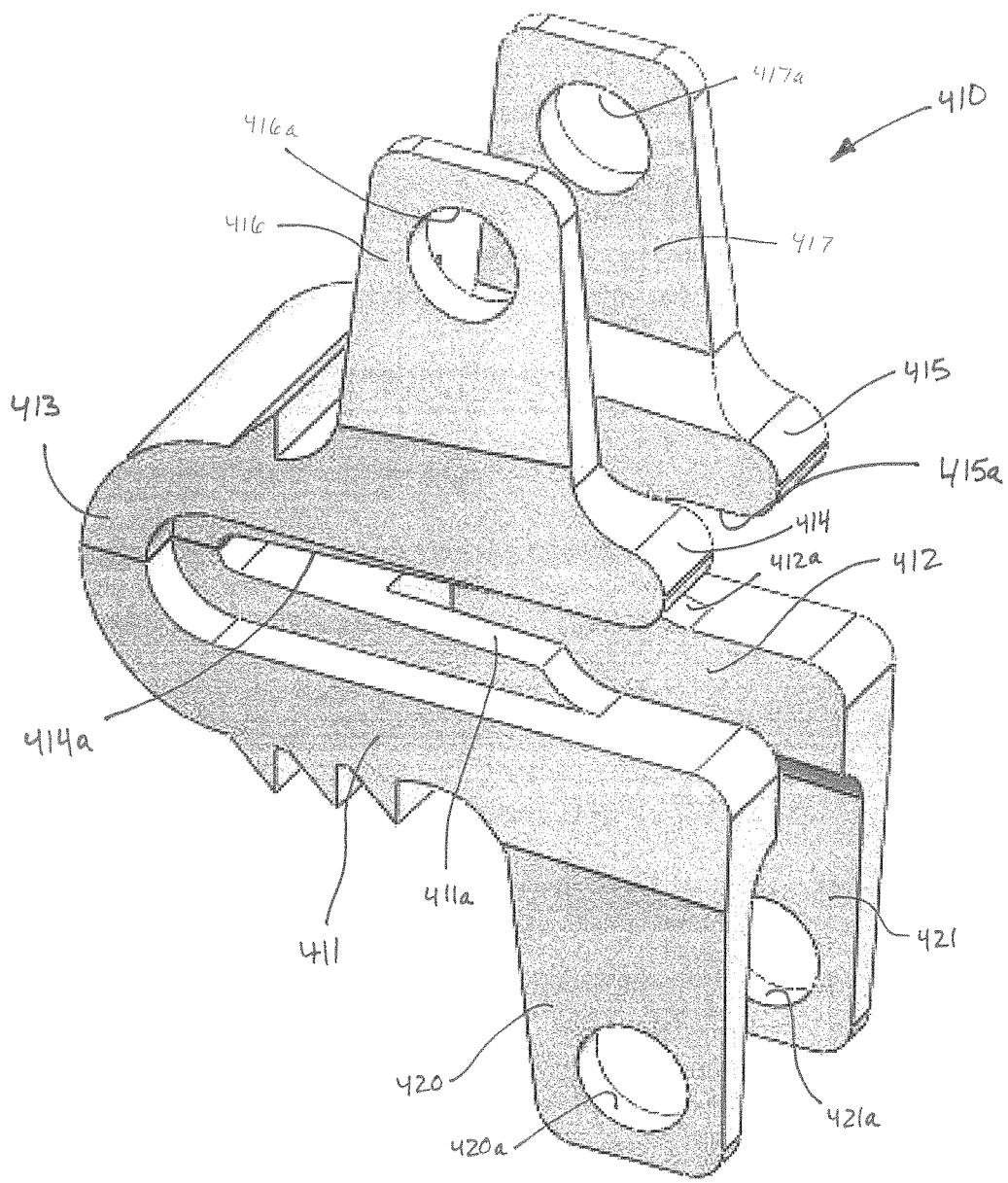
FIG. 27 is a perspective view of a fifth embodiment of an interspinous fusion device in accordance with this invention.
Figure 28:
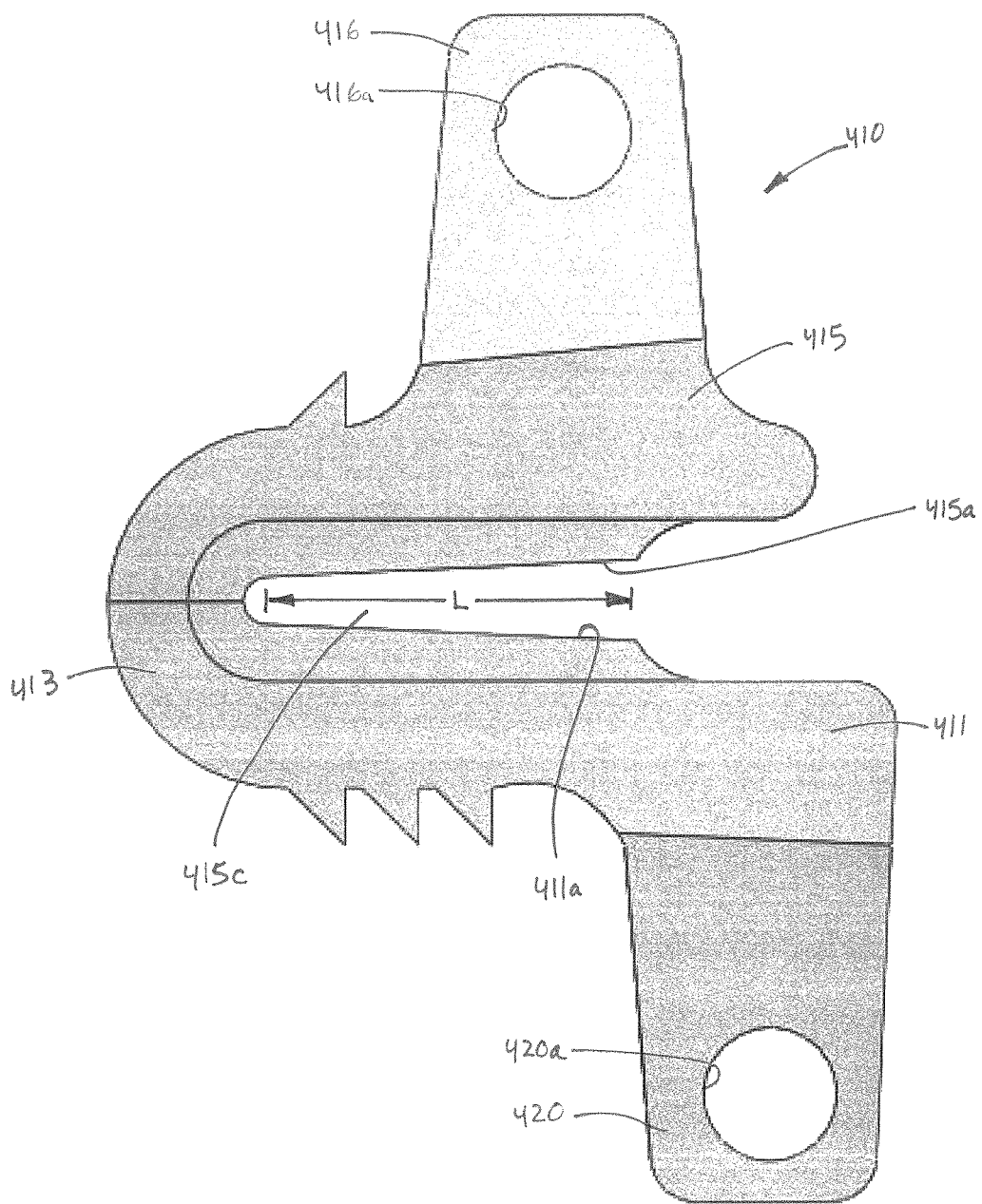
FIG. 28 is a side elevational view of the fifth embodiment of the interspinous fusion device illustrated in FIG. 27.

Referring now to FIGS. 27 and 28, there is illustrated a fifth embodiment of an interspinous fusion device, indicated generally at 410, in accordance with this invention. The fifth embodiment of the interspinous fusion device 410 includes a central body portion that is defined by first and second opposed lower side walls 411 and 412, a rear wall 413, and first and second opposed upper side walls 414 and 415. The first and second opposed lower side walls 411 and 412 have respective upper surfaces 411a and 412a provided thereon, while the first and second opposed upper side walls 414 and 415 have respective lower surfaces 414a and 415a provided thereon. If desired, some or all of the surfaces 411a, 412a, 414a, and 415a may be defined by embossments or other raised structures provided as shown in FIGS. 27 and 28, although such is not required. The first and second opposed lower side walls 411 and 412, the rear wall 413, and the first and second opposed upper side walls 414 and 415 cooperate to define a partially enclosed space, the purpose of which will be explained below.

As best shown in FIG. 28, the rear wall 413 defines a spring-like hinge between the lower side walls 411 and 412 and the upper side walls 414 and 415. A slit 415c (see FIG. 28) or other gap or space is defined between the upper surfaces 411a and 412a of the lower side walls 411 and 412 and the lower surfaces 414a and 415a of the upper side walls 414 and 415. The slit 415c may have any desired shape or size. However, it has been found desirable that the slit 415c have a front-to-rear length L (see FIG. 28) of about 12 mm. As also best shown in FIG. 28, it is desirable that the top-to-bottom height of the slit 415c increases from the rear to the front thereof. The angular relationship between the upper surfaces 411a and 412a of the lower side walls 411 and 412 and the lower surfaces 414a and 415a of the upper side walls 414 and 415 can vary as desired. However, an angular relationship of about 2° has been found to be desirable.

First and second mounting plates 416 and 417 are respectively secured to the upper side walls 414 and 415. The mounting plates 416 and 417 have respective apertures 416a and 417a or other structures provided thereon to facilitate the securement of the interspinous fusion device 410 to an upper one of the pair of adjacent vertebrae, as described above. In the illustrated embodiment, the mounting plates 416 and 417 are each generally planar and extend parallel to one another. However, the mounting plates 416 and 417 may have any desired shape or combination of shapes. Similarly, first and second connecting plates 420 and 421 are respectively secured to the lower side walls 414 and 415. The connecting plates 420 and 421 have respective apertures 420a and 421a or other structures provided thereon to facilitate the securement of the interspinous fusion device 410 to a lower one of the pair of adjacent vertebrae, as also described above. In the illustrated embodiment, the connecting plates 420 and 421 are each generally planar and extend parallel to one another. However, the connecting plates 420 and 421 may have any desired shape or combination of shapes.

Figure 29:
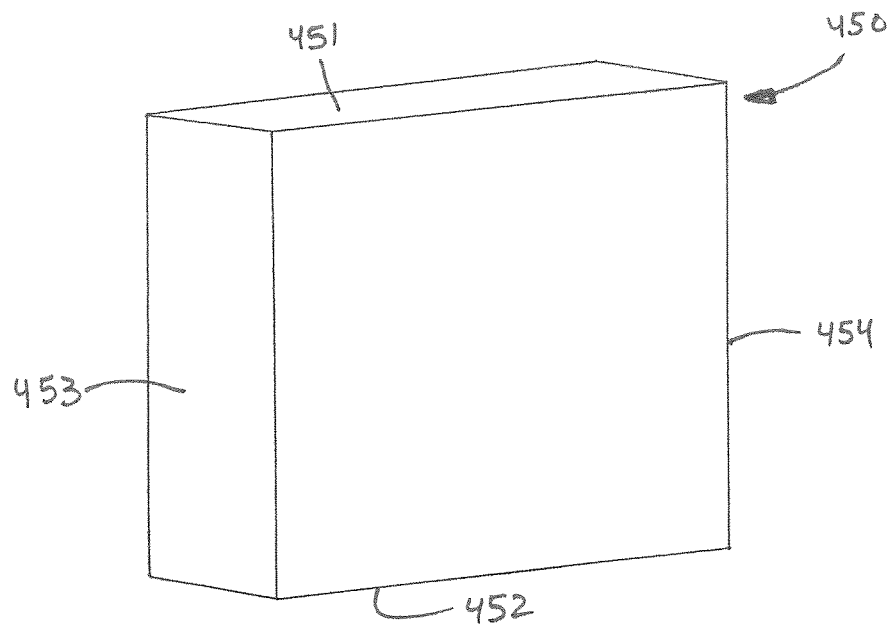
FIG. 29 is a perspective view of a bone graft material that can be used with the fifth embodiment of the interspinous fusion device or any of the other embodiments of the interspinous fusion device described herein.
Figure 30:
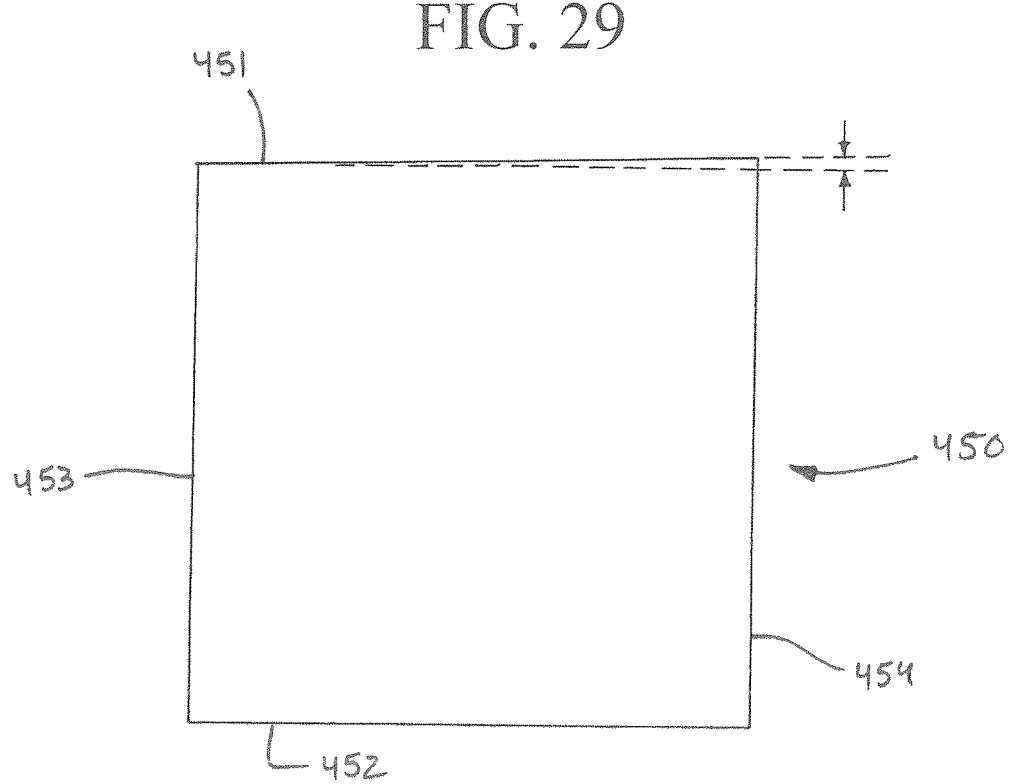
FIG. 30 is a side elevational view of the bone graft material illustrated in FIG. 29.

FIGS. 29 and 30 illustrate a quantity of a bone graft material, indicated generally at 450, that can be used with the fifth embodiment of the interspinous fusion device 410 or any of the other embodiments of the interspinous fusion device described herein. The illustrated bone graft material 450 is generally rectilinear in shape (although such is not required) and includes an upper surface 451, a lower surface 452, a front end 453, and a rear end 454. The bone graft material 450 is adapted to be disposed within the interspinous fusion device 410 with the upper surface 451 adjacent to the lower surfaces 414a and 415a of the upper side walls 414 and 415, the lower surface 452 adjacent to the upper surfaces 411a and 412a of the lower side walls 411 and 412, and the rear end 454 adjacent to the rear wall 413. The angular relationship between the upper and lower surfaces 451 and 452 of the bone graft material 450 can vary as desired. However, as best shown in FIG. 30, the top-to-bottom distance between the upper and lower surfaces 451 and 452 of the bone graft material 450 preferably gets larger from the front end 453 to the rear end 454. The top-to-bottom distance between the upper and lower surfaces 451 and 452 of the bone graft material 450 can, for example, vary in the range of from about 1° to about 5°, preferably about 2°.

The relationship between the size and shape of the gap 415c in the interspinous fusion device 410 and the size and shape of the bone graft material 450 is advantageous. In particular, it is desirable that this relationship be such that a relatively high compression be placed upon the bone graft material 450 while imposing a relatively low stress on the interspinous fusion device 410. The relatively high compression placed upon the bone graft material 450 facilitates that the bone graft material 450 remain in a desired position relative to the interspinous fusion device 410 and, thus, to the vertebrae to which the interspinous fusion device 410 is to be secured. The relatively low stress imposed upon the interspinous fusion device 410 minimizes the likelihood that damage may occur during or after installation of the bone graft material 450. The interspinous fusion device 410 may be formed from any desired material including, but not limited to, polyether ether ketone (PEEK), titanium, nitinol (nickel titanium), cortical bone, and composites.

Figure 31:
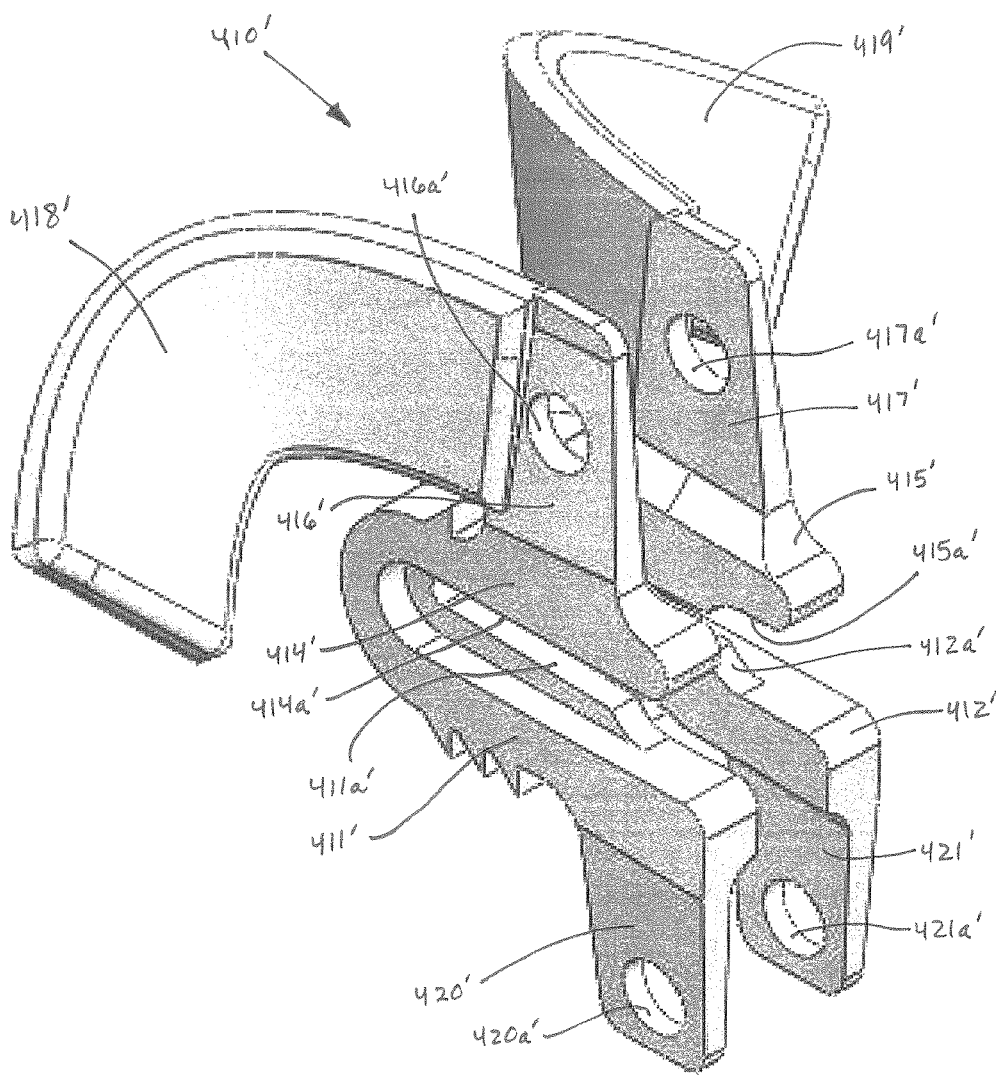
FIG. 31 is a perspective view of a modified version of the fifth embodiment of the interspinous fusion device illustrated in FIGS. 27 and 28.
Figure 32:
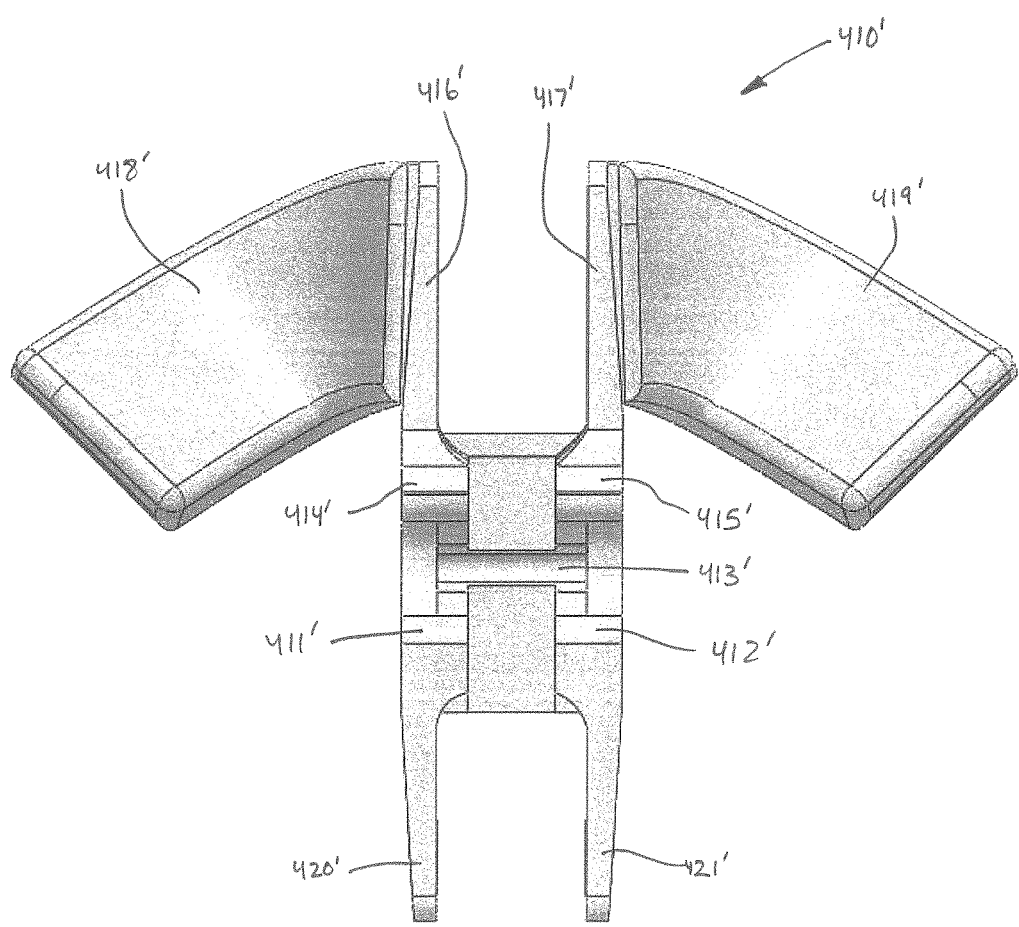
FIG. 32 is a front end elevational view of the modified version of the fifth embodiment of the interspinous fusion device illustrated in FIG. 31.

FIGS. 31 and 32 illustrate a variation 410' on the fifth embodiment of the interspinous fusion device 410 illustrated in FIGS. 27 and 28, and like reference numbers are used to indicate similar structures. In this variation, the interspinous fusion device 410' includes first and second mounting plates 418' and 419' that are respectively secured to the upper ends of the first and second mounting plates 416' and 417'. Like the various mounting plates discussed above, the first and second mounting plates 418' and 419' may have any desired shape or combination of shapes, may be fixed in position relative to the respective mounting plates 416' and 417' (as illustrated) or movable relative thereto (such as shown in FIGS. 6 through 18), and may include one or more apertures (not shown) to facilitate the securement of the interspinous fusion device 410' to respective ones of the upper pair of adjacent vertebrae, all as described above.

Figure 33:
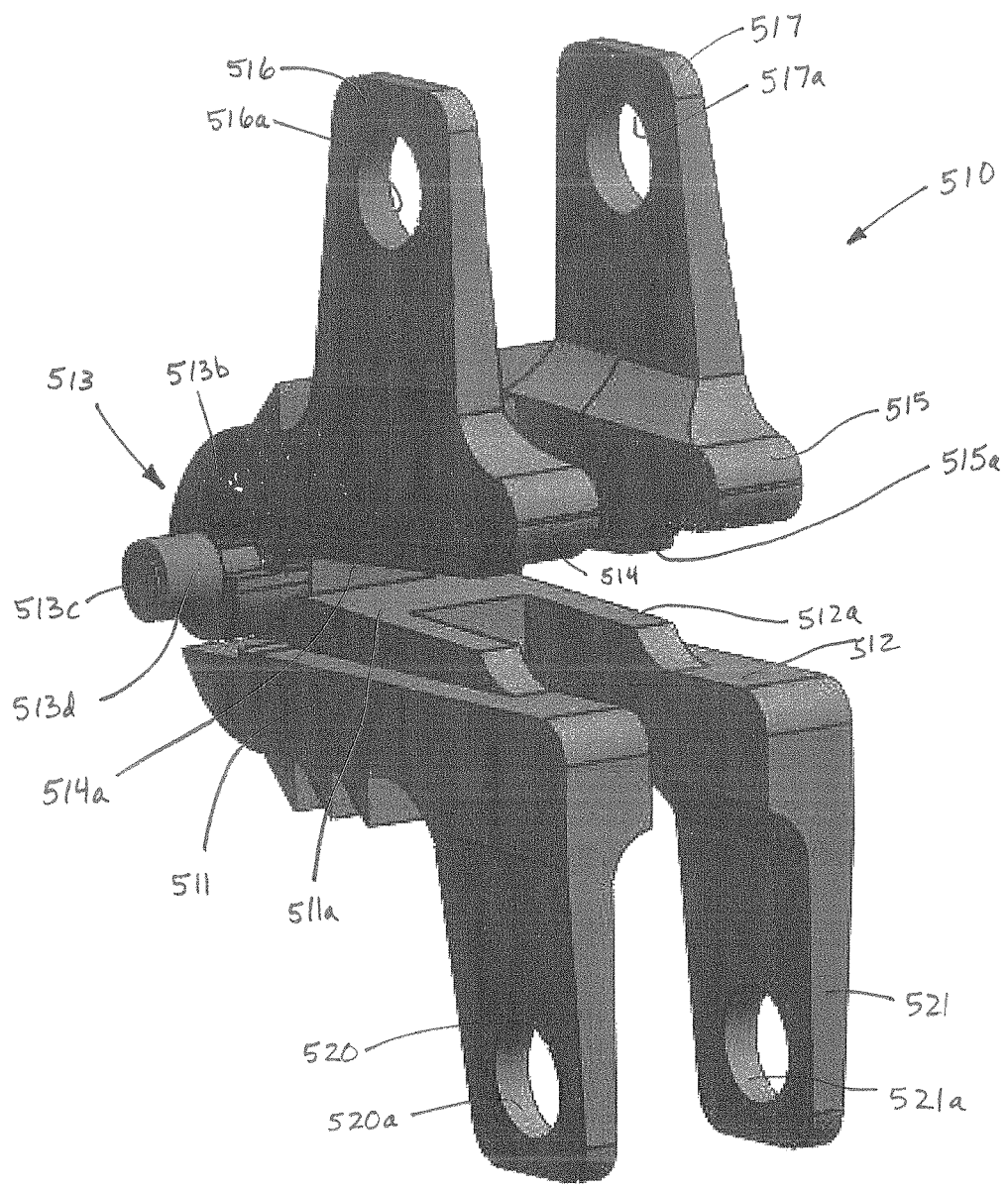
FIG. 33 is a perspective view of a sixth embodiment of an interspinous fusion device in accordance with this invention.
Figure 34:
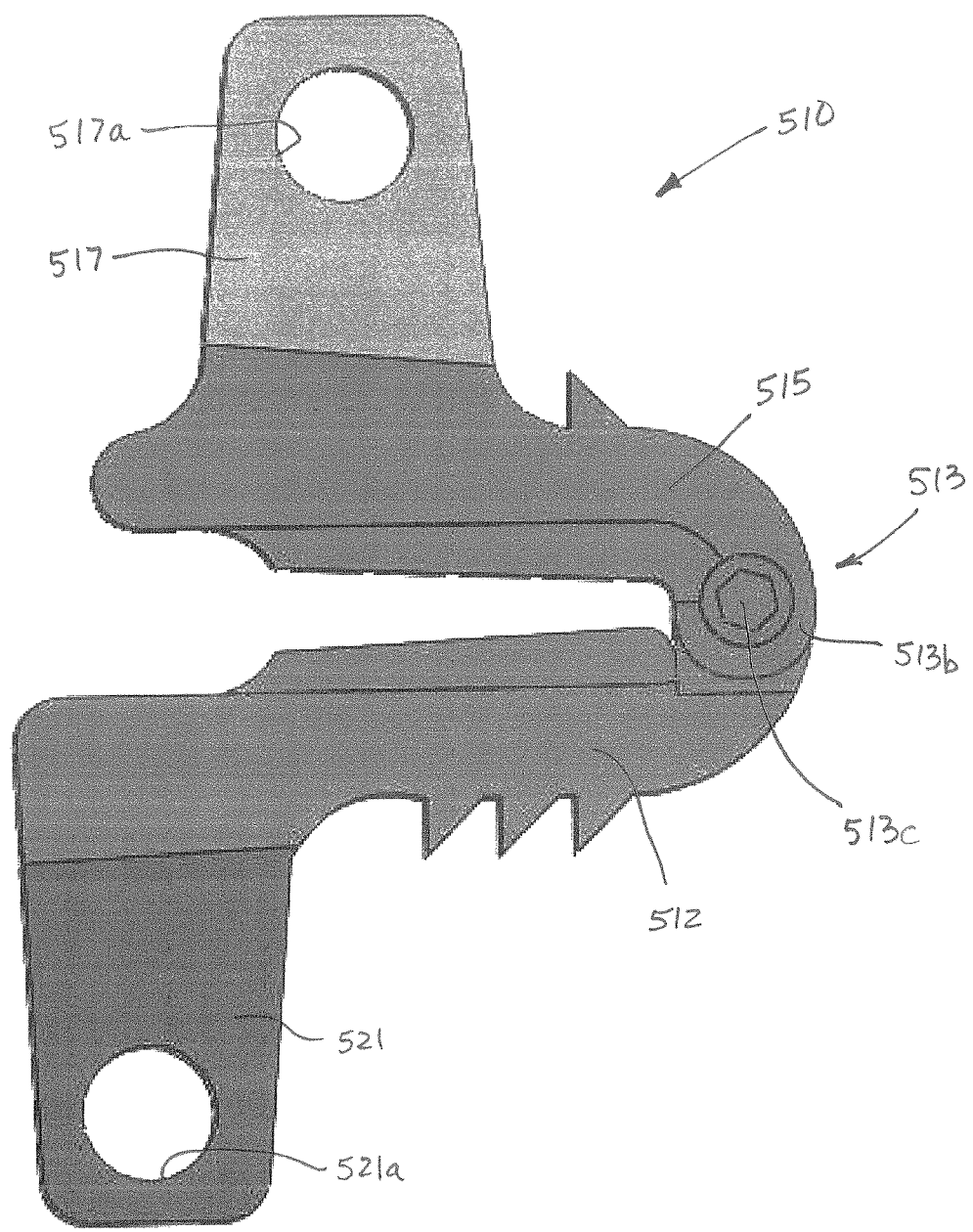
FIG. 34 is a side elevational view of the sixth embodiment of the interspinous fusion device illustrated in FIG. 33.
Figure 35:
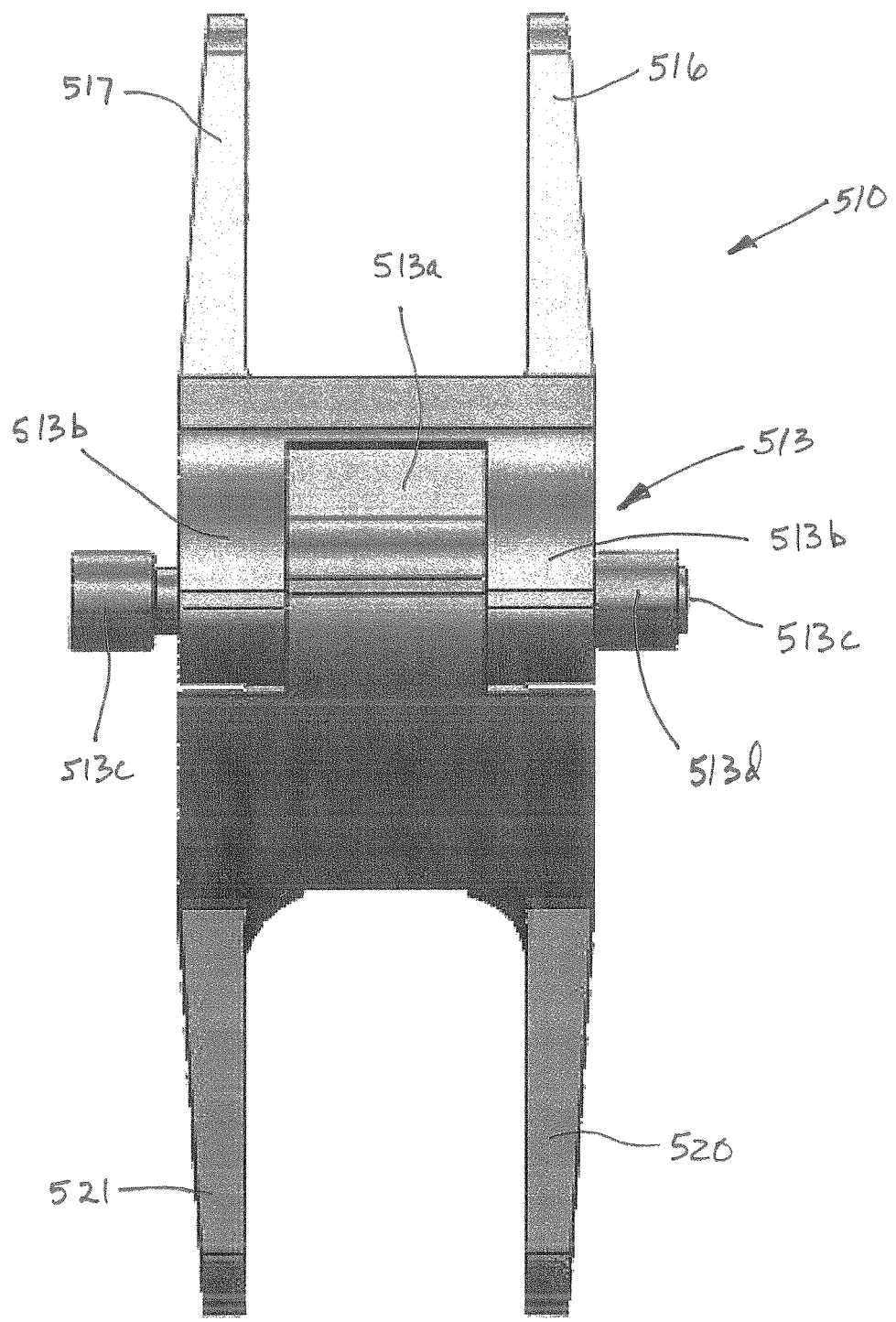
FIG. 35 is a rear end elevational view of the sixth embodiment of the interspinous fusion device illustrated in FIGS. 33 and 34.

Referring now to FIGS. 33 through 35, there is illustrated a sixth embodiment of an interspinous fusion device, indicated generally at 510, in accordance with this invention. The sixth embodiment of the interspinous fusion device 510 is similar to the fourth embodiment of the interspinous fusion device 410 described above, and like reference numbers (incremented by 100) are used to indicate similar structures. In this sixth embodiment of the interspinous fusion device 510, however, the rear wall of the interspinous fusion device 510 is defined by a hinge, indicated generally at 513, that includes a first portion 513a that is formed integrally with or connected to the lower side walls 511 and 512 and a second portion 513b that is formed integrally with or connected to the lower side walls 511 and 512. A pivot pin 513c extends through aligned apertures (not shown) formed through the first and second portions 513a and 513b such that the lower side walls 511 and 512 can pivot relative to the upper side walls 514 and 515 in a jaw-like manner. A locking nut 513d may be threaded onto the end of (or otherwise secured to) the pivot pin 513c. The locking nut 513d can be selectively operated (typically tightened on the pivot pin 513c) so as to retain the lower side walls 511 and 512 in a desired position relative to the upper side walls 514 and 515.

In use, the sixth embodiment of the interspinous fusion device 510 is installed by initially releasing the locking nut 513d so that the lower side walls 511 and 512 are free to pivot relative to the upper side walls 514 and 515. Then the interspinous fusion device 510 is installed by securing the mounting plates 416 and 417 to an upper one of the pair of adjacent vertebrae, and further by securing the connecting plates 420 and 421 to a lower one of the pair of adjacent vertebrae, as also described above. Thereafter, the locking nut 513d is tightened on the pivot pin 513c so as to maintain the lower side walls 511 and 512 in a predetermined position relative to the upper side walls 514 and 515. This structure allows the spacing between the first and second opposed lower side walls 511 and 512 and the first and second opposed upper side walls 514 and 515 to be customized to the specific anatomy of the patient.

Figure 36:
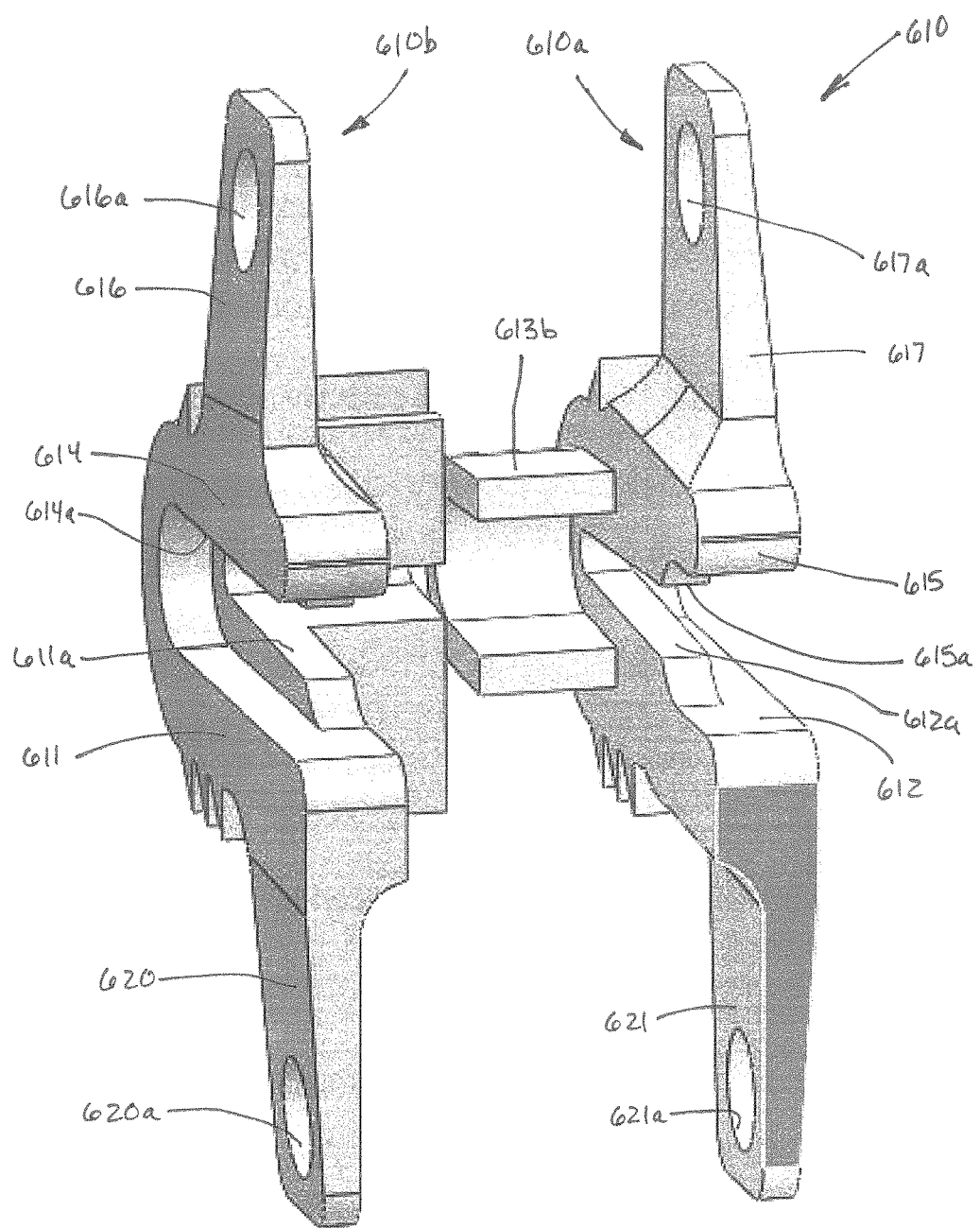
FIG. 36 is an exploded perspective view of a seventh embodiment of an interspinous fusion device in accordance with this invention.
Figure 37:
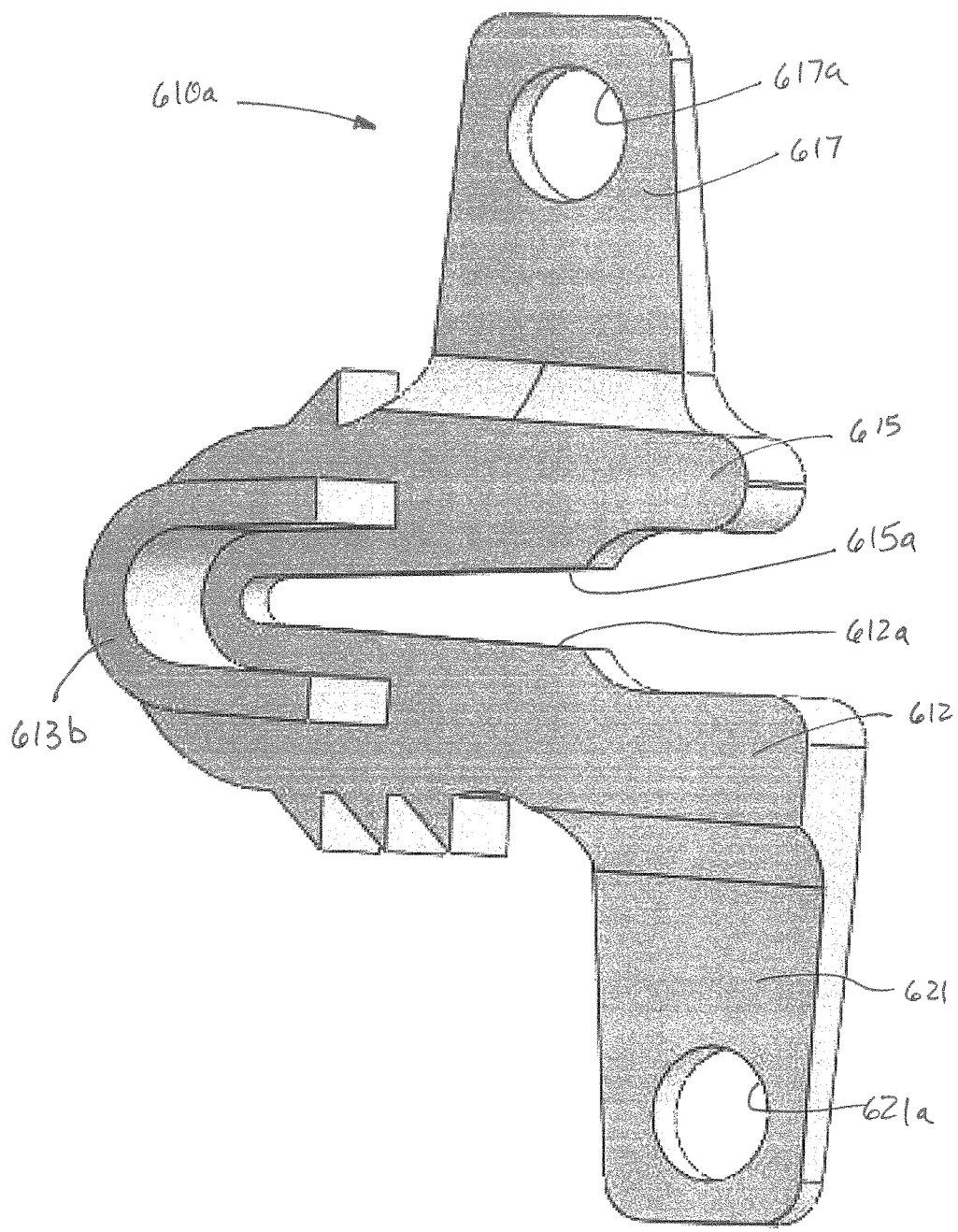
FIG. 37 is a perspective view of a first portion of the seventh embodiment of an interspinous fusion device illustrated in FIG. 36.
Figure 38:
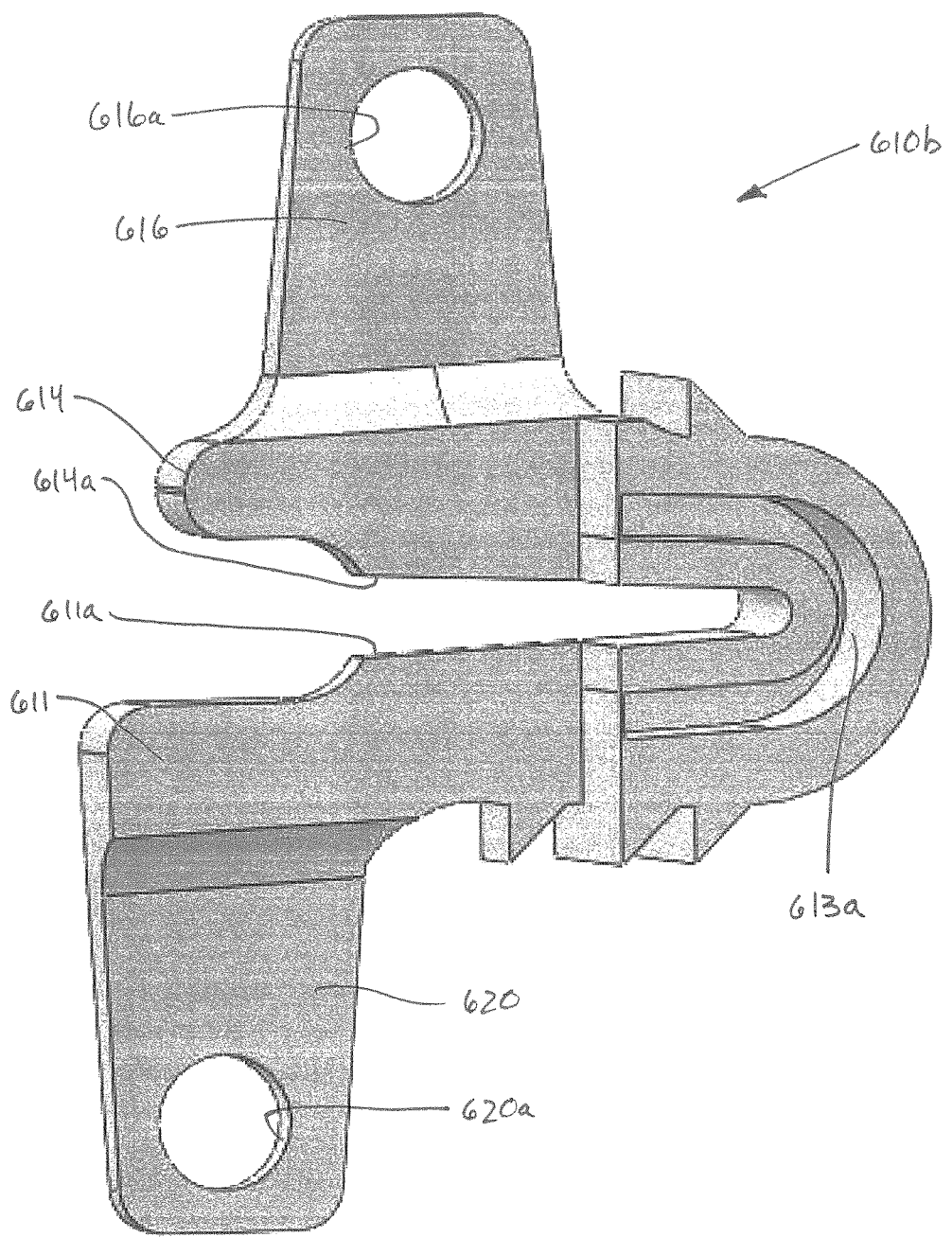
FIG. 38 is a perspective view of a second portion of the seventh embodiment of an interspinous fusion device illustrated in FIGS. 36 and 37.

Referring now to FIGS. 36 through 38, there is illustrated a seventh embodiment of an interspinous fusion device, indicated generally at 610, in accordance with this invention. The seventh embodiment of the interspinous fusion device 610 is similar to the fourth embodiment of the interspinous fusion device 410 described above, and like reference numbers (incremented by 200) are used to indicate similar structures. In this seventh embodiment, however, the interspinous fusion device 610 is split into two separate lateral portions 610a and 610b that are supported on one another. To accomplish this, the first portion 610a has a protrusion 613b provided thereon that extends laterally toward the second portion 610b of the interspinous fusion device 610. Similarly, the second portion 610a has a recess 613a provided thereon that faces laterally toward the first portion 610a of the interspinous fusion device 610. Preferably, the recess 613a and the protrusion 613b are sized and shaped in a complementary manner, such as the illustrated U-shaped configurations. However, the recess 613a and the protrusion 613b may be formed having any desired sizes and shapes, as well as combinations thereof.

The interspinous fusion device 610 is assembled by initially aligning the protrusion 613b provided on the first portion 610a with the recess 613a provided on the second portion 610b as shown in FIG. 36. Then, the first and second portions 610a and 610b are moved toward one another such that the protrusion 613b is received within the recess 613a. Preferably, the recess 613a and the protrusion 613b are sized and shaped so that relative lateral movement is permitted without significant other looseness therebetween. This structure allows the lateral spacing between the mounting plates 616 and 617 and/or between the connecting plates 620 and 621 to be customized to the specific anatomy of the patient. If desired, a locking mechanism (not shown) can be provided to maintain the first and second portions 610a and 610b in a desired lateral orientation relative to one another.

The principle and mode of operation of this invention have been explained and illustrated in its various embodiments. However, it must be understood that this invention may be practiced otherwise than as specifically explained and illustrated without departing from its spirit or scope.

What is claimed is:

1. An interspinous stabilization device comprising:
   a body portion having a first end and a second end, the body portion comprising a rear wall at the first end connected to opposed upper side walls and opposed lower side walls, and a slit extending between upper surfaces of the lower side walls and lower surfaces of the upper side walls, wherein the opposed upper side walls are unconnected except at the first end, and the opposed lower side walls are unconnected except at the first end;
   a pair of mounting plates supported on the body portion and adapted to engage a first vertebra; and
   a pair of connecting plates supported on the body portion and adapted to engage a second vertebra, wherein the connecting plates have respective apertures;
   wherein the rear wall defines a spring-like hinge between the pair of mounting plates and the pair of connecting plates; and
   wherein the interspinous stabilization device is adapted to maintain continued axial loading of a graft disposed between the first and second vertebra as settling of the graft occurs.

2. The interspinous stabilization device defined in claim 1 wherein the interspinous fusion device is split into two separate lateral portions that are supported on one another.

3. The interspinous stabilization device of claim 1, wherein the connecting plates are generally planar and extend parallel to each other.

4. The interspinous stabilization device of claim 1, wherein the slit continuously expands in height directly from the rear wall.

5. An interspinous stabilization device comprising:
   a body portion comprising first and second opposed lower side walls having upper surfaces, a rear wall, and first and second opposed upper side walls having lower surfaces;
   a pair of mounting plates supported on the body portion and adapted to engage a first vertebra;
   a pair of connecting plates supported on the body portion and adapted to engage a second vertebra; and
   a slit extending from the rear wall between the pair of mounting plates and the pair of connecting plates, wherein the slit continuously expands in height directly from the rear wall;
   wherein the interspinous stabilization device is adapted to maintain continued axial loading of a graft disposed between the first and second vertebra as settling of the graft occurs.

6. The interspinous stabilization device of claim 5, wherein the connecting plates are generally planar and extend parallel to each other.

7. The interspinous stabilization device of claim 5, wherein the connecting plates have respective apertures.

8. An interspinous stabilization device comprising:
   a body portion comprising a rear wall connected to opposed upper side walls and opposed lower side walls, and a slit extending from a rear at the rear wall to a front, and between upper surfaces of the lower side walls and lower surfaces of the upper side walls, wherein the slit has a height between the upper surfaces and the lower surfaces that continuously increases directly from the rear wall to the front;
   a pair of mounting plates supported on the body portion and adapted to engage a first vertebra; and a pair of connecting plates supported on the body portion and adapted to engage a second vertebra;

wherein the rear wall defines a spring-like hinge between the pair of mounting plates and the pair of connecting plates; and wherein the interspinous stabilization device is adapted to maintain continued axial loading of a graft disposed between the first and second vertebra as settling of the graft occurs.

9. The interspinous stabilization device of claim 8, wherein the connecting plates are generally planar and extend parallel to each other.

10. The interspinous stabilization device of claim 8, wherein the connecting plates have respective apertures.

* * * * *